US012648840B2

(12) United States Patent
Midha et al.

(10) Patent No.: US 12,648,840 B2
(45) Date of Patent: Jun. 9, 2026

(54) PROSTHETIC HEART VALVE PACKAGING AND ATTACHMENT ASSEMBLY

(71) Applicant: Cephea Valve Technologies, Inc., Abbott Park, IL (US)

(72) Inventors: Prem Midha, St. Paul, MN (US); Zachary R. Vidlund, Robbinsdale, MN (US); Eric Smith, Minneapolis, MN (US)

(73) Assignee: Cephea Valve Technologies, Inc., Abbott Park, IL (US)

( * ) Notice: Subject to any disclaimer, the term of this patent is extended or adjusted under 35 U.S.C. 154(b) by 76 days.

(21) Appl. No.: 18/702,565

(22) PCT Filed: Dec. 14, 2022

(86) PCT No.: PCT/US2022/081513
§ 371 (c)(1),
(2) Date: Apr. 18, 2024

(87) PCT Pub. No.: WO2023/114817
PCT Pub. Date: Jun. 22, 2023

(65) Prior Publication Data
US 2025/0275845 A1       Sep. 4, 2025

Related U.S. Application Data

(60) Provisional application No. 63/289,718, filed on Dec. 15, 2021.

(51) Int. Cl.
*A61F 2/00*        (2006.01)
*A61F 2/24*        (2006.01)

(52) U.S. Cl.
CPC .............. *A61F 2/0095* (2013.01); *A61F 2/24* (2013.01)

(58) Field of Classification Search
CPC ........ A61F 2/0095; A61F 2/24; A61F 2/2418; A61F 2220/0033; A61F 2220/0075; A61F 2/9525
See application file for complete search history.

(56) References Cited

U.S. PATENT DOCUMENTS

| | | | |
|---|---|---|---|
| 10,722,357 B2 * | 7/2020 | High | A61F 2/2418 |
| 11,701,214 B2 * | 7/2023 | Haynes | A61F 2/0095 623/2.11 |
| 11,896,486 B2 | 2/2024 | Pasquino | |

(Continued)

FOREIGN PATENT DOCUMENTS

| | | |
|---|---|---|
| WO | 2014085040 A1 | 6/2014 |
| WO | 2017222669 A1 | 12/2017 |
| WO | 2018067788 A1 | 4/2018 |

*Primary Examiner* — Andrew D Perreault
(74) *Attorney, Agent, or Firm* — SLEMAN & LUND LLP

(57) ABSTRACT

A system for heart valve replacement includes a collapsible and expandable replacement heart valve and a packaging assembly for storing the replacement heart valve. The packaging assembly includes a funnel extending from a first end to a second end. The funnel has a first interior diameter at the first end and a second interior diameter, the second interior diameter smaller than the first interior diameter. The funnel defines an internal lumen extending between the first and second ends. The funnel defines a plurality of longitudinal slots extending along an interior surface of the funnel between the first and second ends.

13 Claims, 25 Drawing Sheets

(56)     References Cited

U.S. PATENT DOCUMENTS

2010/0101682  A1*    4/2010   Barber .................... B65B 23/00
                                                                    141/331
2019/0117394  A1      4/2019   Morin
2020/0170792  A1*    6/2020   Morin ................... A61F 2/2427
2021/0361404  A1     11/2021   Haynes
2022/0313428  A1     10/2022   Bergin \* cited by examiner

PROSTHETIC HEART VALVE PACKAGING AND ATTACHMENT ASSEMBLY

CROSS-REFERENCE TO RELATED APPLICATIONS

This application is a national stage entry of PCT/US2022/081513, filed Dec. 14, 2022, and claims the benefit of the filing date of U.S. Provisional Patent Application No. 63/289,718, filed Dec. 15, 2021, the disclosures of each of which is are hereby incorporated herein by reference.

BACKGROUND OF THE DISCLOSURE

A primary treatment for heart valve disease is valve replacement. One form of replacement device is a bio-prosthetic replacement valve, particularly those designed for a minimally invasive procedure. Following manufacture of the valve and prior to implantation, the replacement heart valve is packaged and transported to the site of use. Typically, replacement heart valves may be packaged in liquid-filled jars or dry air-tight containers. The replacement heart valve preferably is held stationary relative to the jar or packaging to prevent or minimize damage to the replacement heart valve.

Prior to implantation, the replacement heart valve is removed from the jar and may be rinsed to remove any shipment fluid or clean the valve assembly. The replacement heart valve for a minimally invasive procedure may be collapsed and assembled to a delivery system for placement in the patient. However, rinsing and assembling the replacement heart valve to the delivery system are performed by a practitioner which requires skill and time and can lead to human error. Further, several separate tools and devices, such as a funnel or crimping device, may be required to collapse the valve into the delivery system, which may crowd the operation space and require a number of additional steps for placement, attachment, and use of the funnel.

Thus, further developments in the field of packaging and collapsing the valve into the delivery device are desired.

BRIEF SUMMARY OF THE DISCLOSURE

According to a first aspect of the disclosure, a system for heart valve replacement includes a collapsible and expandable replacement heart valve and a packaging assembly. The packaging assembly may be used to store the replacement heart valve. The packaging assembly may include a funnel. The funnel may extend from a first end to a second end. The funnel may have a first interior diameter at the first end and a second interior diameter at the second end, the second interior diameter being smaller than the first interior diameter. The funnel may define an internal lumen extending between the first and second ends. The funnel may define a plurality of longitudinal slots extending along an interior surface of the funnel between the first and second ends.

According to another aspect of the disclosure, a packaging assembly for packaging a collapsible and expandable replacement heart valve may include a valve support, a funnel and a retention mechanism. The valve support may have a base. The funnel may be detachably coupleable to the valve support. The funnel may define a lumen configured to receive the replacement heart valve. The retention mechanism may include a pin extending through a lumen of the valve support and a plurality of sutures attached to the pin. The plurality of sutures may be configured to be attached to the replacement heart valve.

According to another aspect of the disclosure, a system for heart valve replacement may include a packaging assembly for storing a collapsible and expandable replacement heart valve. The packaging assembly may include a funnel. The funnel may extend from a first end to a second end. The funnel may have a first inner diameter at the first end and a second inner diameter at the second end. The second inner diameter may be smaller than the first inner diameter. The funnel may define an internal lumen extending between the first and second ends. The funnel may define a plurality of longitudinal slots extending along an inner surface of the funnel between the first and second end.

According to another aspect of the disclosure, a method of packaging a replacement heart valve may include the steps of positioning the replacement heart valve within a funnel; coupling the funnel to a valve support; and coupling a retention mechanism to the replacement heart valve to hold the valve in position relative to the valve support and the funnel. The replacement heart valve, the funnel, the valve support, and the retention mechanism together may form a packaging assembly.

According to another aspect of the disclosure, a method of packaging a replacement heart valve may include the steps of positioning the replacement heart valve within a ring such that the ring circumferentially surrounds a central portion of the replacement heart valve; coupling the ring to a funnel by engaging locking tabs of the ring with corresponding securement members of the funnel; and coupling the ring to a valve support by engaging locking tabs of the ring with corresponding ledges of the valve support.

According to another aspect of the disclosure, a method of loading a replacement heart valve from a packaging assembly into a delivery device may include the steps of providing a packaging assembly including a replacement heart valve positioned within a funnel, the replacement heart valve having a plurality of tines aligned with corresponding slots of the funnel; coupling the packaging assembly to the delivery device; translating the replacement heart valve through the funnel and the tines through the slots to collapse the replacement heart valve from an expanded condition to a collapsed condition; and transitioning the replacement heart valve from the funnel to the delivery device.

DETAILED DESCRIPTION

The packaging assemblies of the present disclosure hold a replacement heart valve securely in a shipment jar or packaging container and optionally allow for pre-tensioning of components of the replacement valve assembly such that the replacement valve is secured and tensioned in the packaging during shipment. The packaging assembly further allows the valve to be transitioned from a packaged (e.g., expanded) configuration to a delivery (e.g., collapsed) configuration by translating the valve through a funnel included in the packaging assembly to be inserted into a delivery device and prepared for delivery. The funnel may be constructed as part of the packaging assembly, which serves to protect the replacement valve within the packaging and also reduces the complexity of the procedure when loading the valve into a delivery device.

Figure 1A:
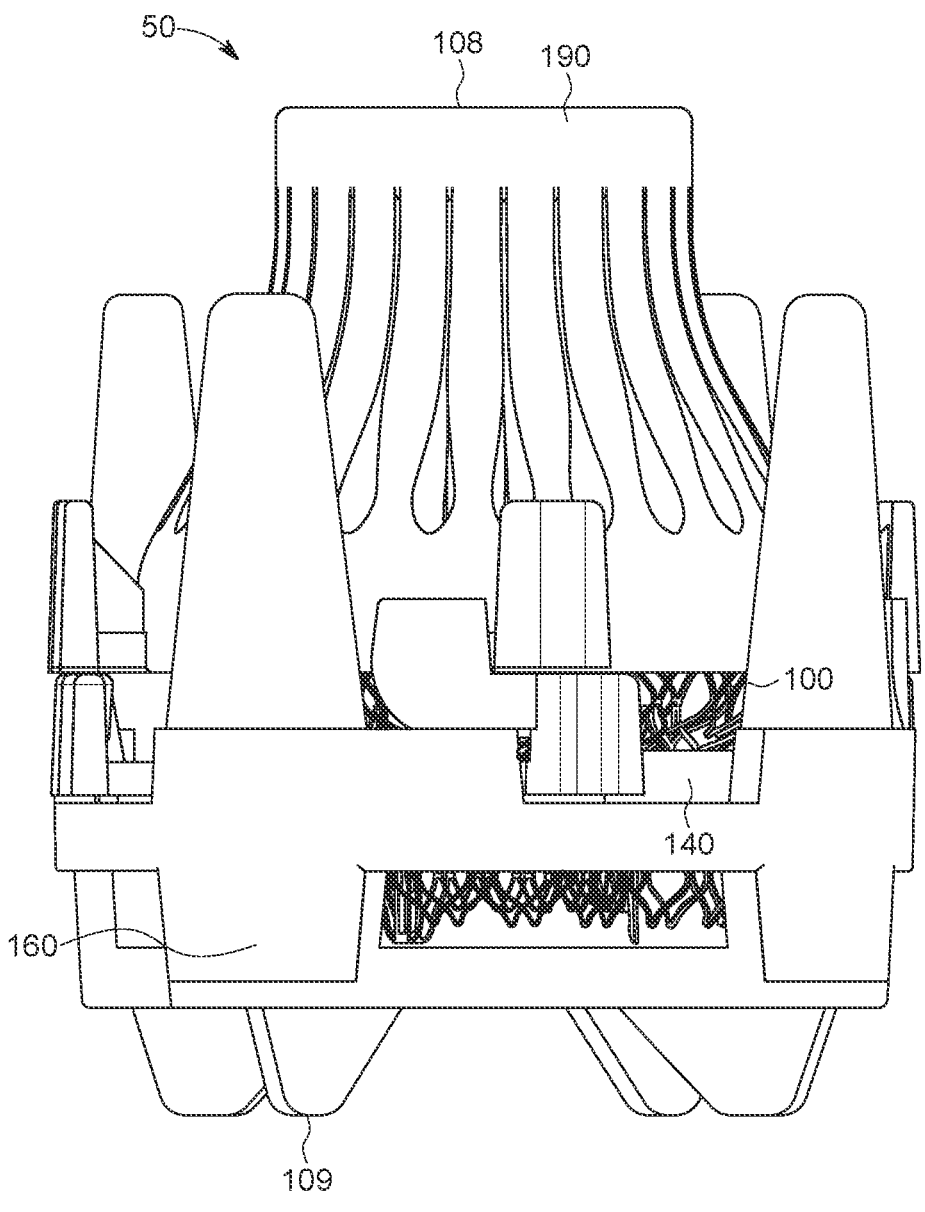
FIG. 1A is a front view of a packaging assembly according to an embodiment of the disclosure.
Figure 1B:
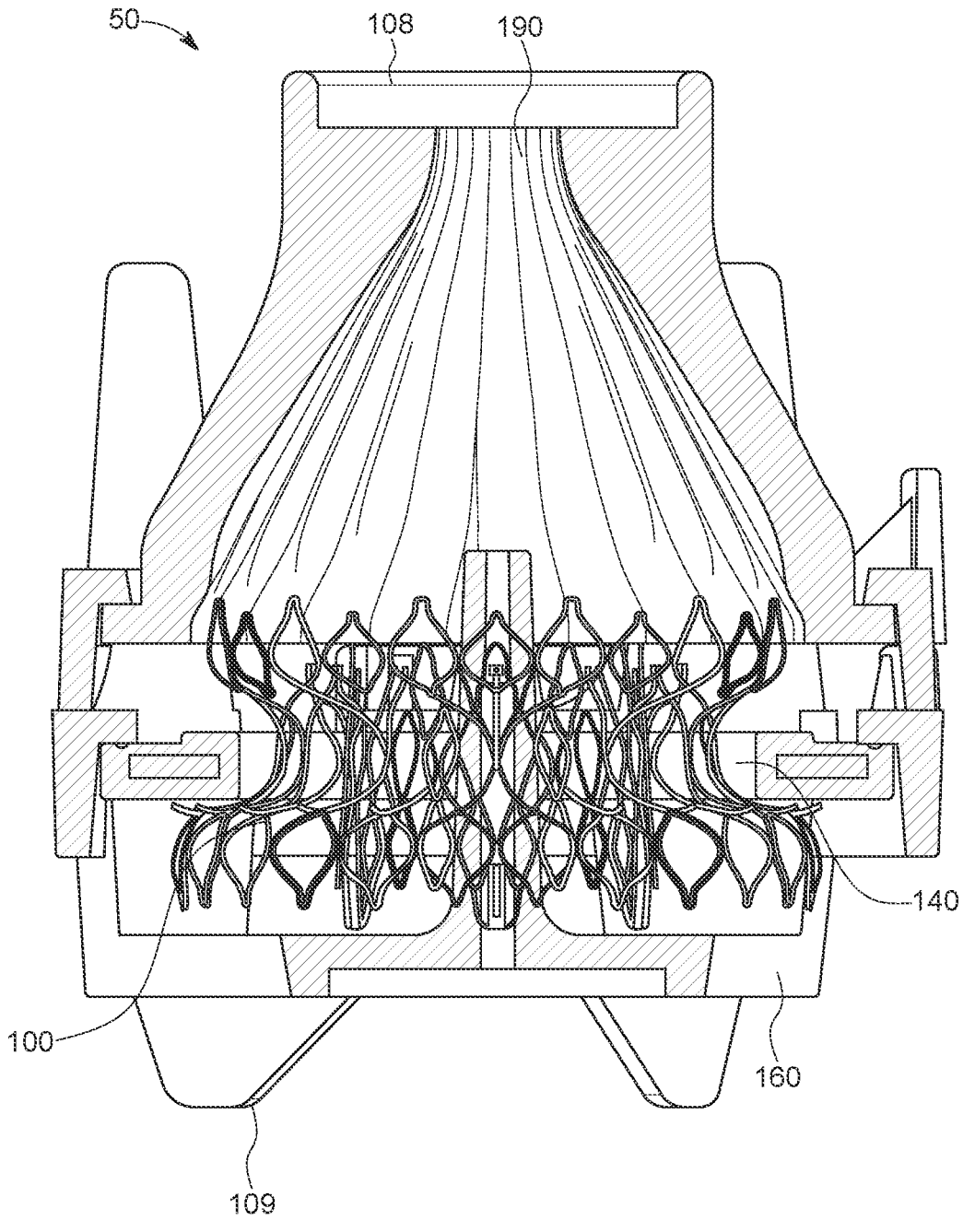
FIG. 1B is a cut-away view of the packaging assembly of FIG. 1A.
Figure 1C:
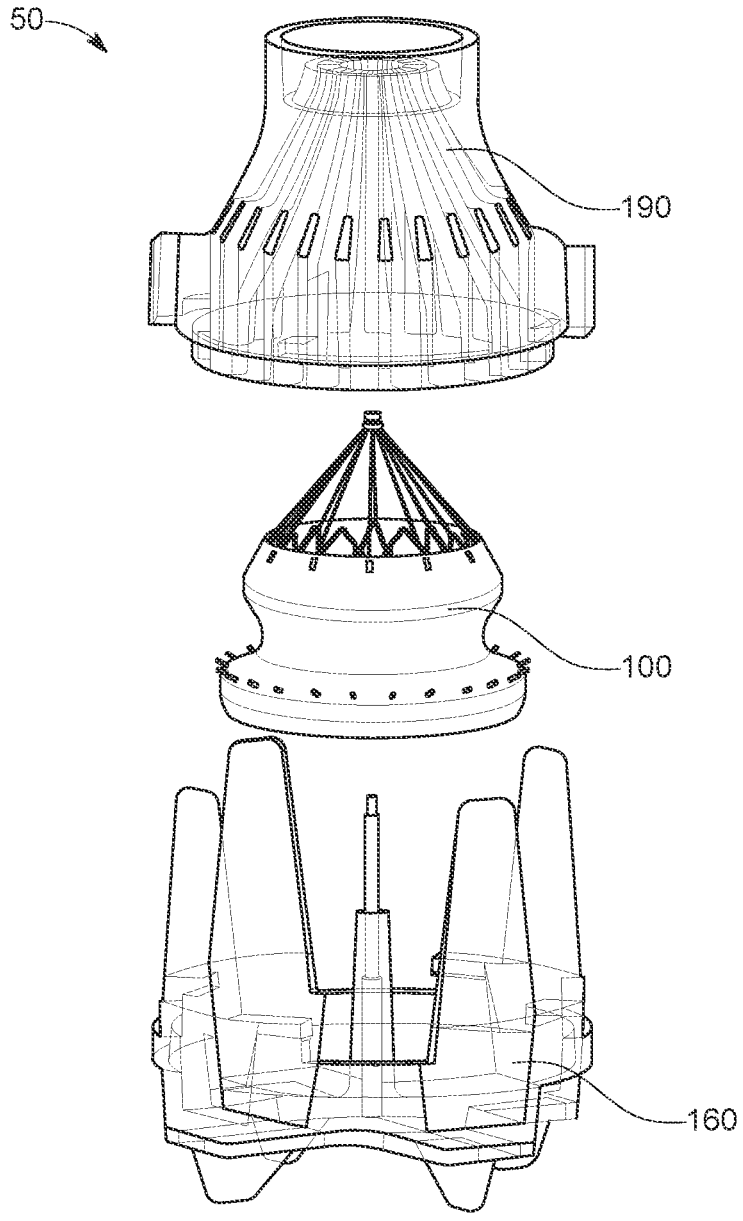
FIG. 1C is an exploded view of a packaging assembly, similar to the packaging assembly of FIG. 1B, in which the replacement heart valve is covered by a fabric skirt.

A fully assembled packaging assembly 50 according to an embodiment of the disclosure is shown in FIGS. 1A-1B. Packaging assembly 50 includes replacement heart valve 100, valve support 160, ring 140, and funnel 190. Each component is described below in detail. For ease of illustration throughout the disclosure, packaging assembly 50 is described herein extending from proximal end 108 to distal end 109, wherein when the valve is being transitioned from the packaging assembly to a delivery device, the assembly will be oriented such that the proximal end abuts the delivery device and the distal end is farther away from the opening of the delivery device. In the particular illustrated example, the proximal end is synonymous with an inflow end of the replacement heart valve 100, and the distal end is synonymous with an outflow end of the replacement heart valve 100. However, it should be understood that the terms proximal and distal are solely used for convenience, and need not correspond to any particular directionality unless otherwise noted herein. For a clearer view of the components of packaging assembly 50, FIG. 1C shows an exploded view of the assembly, although it should be noted that the exploded view does not include ring 140. Certain embodiments described in the present disclosure may include a ring, and some may not. An exemplary prosthetic heart valve packaging and attachment assembly is described in U.S. Patent Application Publication US 2021/0361404, filed on May 11, 2021, and entitled PROSTHETIC HEART VALVE PACKAGING AND ATTACHMENT ASSEMBLY, the disclosure of which is hereby incorporated by reference herein in its entirety.

Figure 2A:
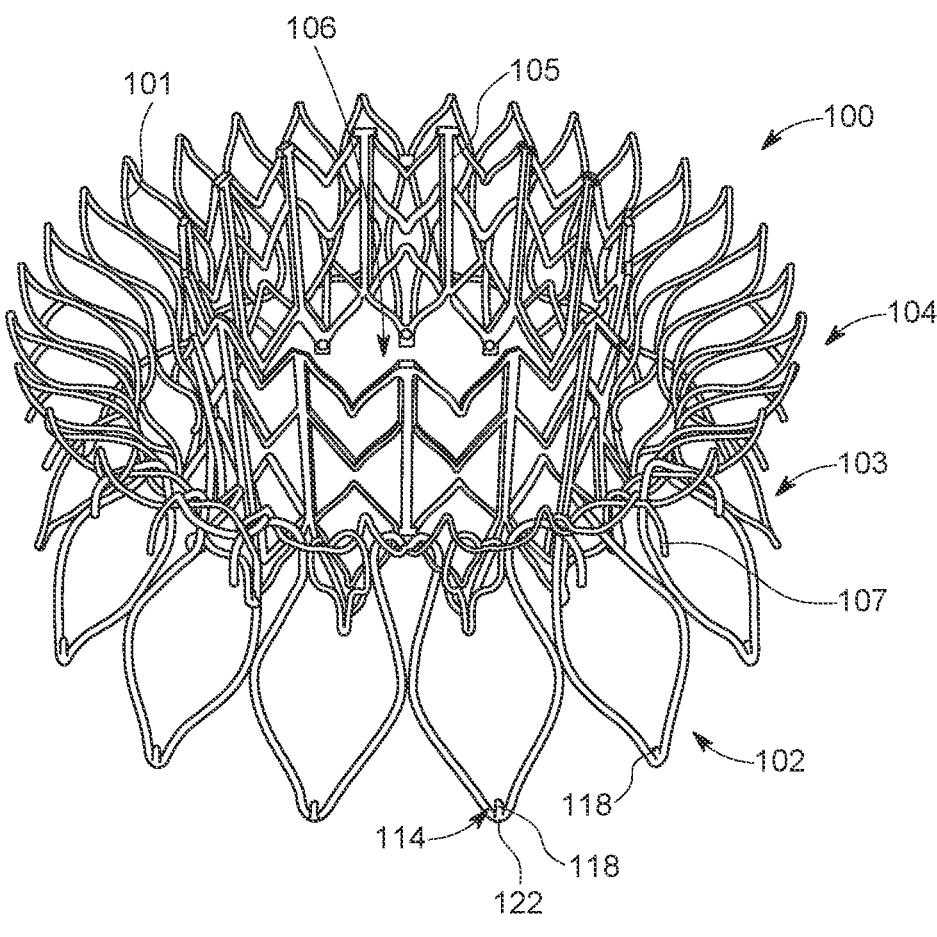
FIG. 2A is a perspective view of a frame of a replacement heart valve that may be used with the packaging assembly of FIG. 1A.
Figure 2B:
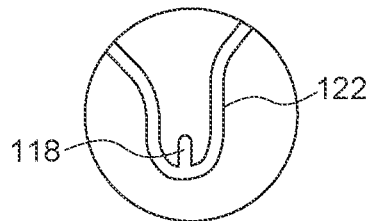
FIG. 2B is an enlarged view of an attachment member of the replacement heart valve of FIG. 2A.

The packaging assemblies of the present disclosure may be used with replacement heart valves, such as replacement heart valve 100 shown more clearly in FIGS. 2A-2B, which is an expandable (e.g. self-expandable) prosthetic implant having an expanded configuration and a collapsed configuration. Replacement heart valve 100 may be a replacement mitral valve having a stent that includes an anchor assembly (e.g. for anchoring the replacement heart valve 100 within the native valve annulus) and a strut frame (e.g. for supporting prosthetic valve leaflets) disposed within the anchor assembly. However, replacement heart valve 100 may be suitable for use in replacing other native heart valves, such as the tricuspid valve, aortic valve, or pulmonary valve, although it may be best suited for replacing the atrioventricular valves. Anchor assembly 101 includes atrial anchor 102, ventricular anchor 104 and central portion 103 positioned axially between the atrial and ventricular anchors. Atrial anchor 102 is configured to be positioned on an atrial side of a mitral valve annulus, and ventricular anchor 104 is configured to be positioned on a ventricular side of the mitral valve annulus. Within packaging assembly 50, atrial anchor 102 is positioned relatively closer to proximal end 108 and ventricular anchor 104 is positioned relatively closer to distal end 109. Anchor assembly 101 may have an hour glass shape in that each of atrial anchor 102 and ventricular anchor 104 flares radially outward of central portion 103, such that the central portion defines a waist between the atrial anchor and the ventricular anchor. Anchor assembly 101 includes tines 107 having traumatic tips and extending generally radially outward proximate to ventricular anchors 104. Tines 107 promote secure implantation of valve 100 into a native valve annulus of a patient by anchoring into the surrounding tissue. Replacement heart valve 100 may also include strut frame 105 positioned radially inward of anchor assembly 101 and formed of a plurality of connected struts. The radially inner surfaces of strut frame 105 define a perimeter of central opening 106, which allows blood to flow through replacement heart valve 100 in the antegrade direction. Exemplary replacement heart valves are described in U.S. Pat. No. 10,470,881, the disclosure of which is hereby incorporated by reference herein in its entirety.

Replacement heart valve 100 includes one or more prosthetic leaflets (not shown). The leaflets may be secured to an interior of strut frame 105 and may be disposed at least partially in central opening 106. The prosthetic leaflets are configured to coapt with each other in order to control blood flow therethrough, allowing blood to flow from in a direction from atrial anchor 102 toward ventricular anchor 104 (the antegrade direction), but to substantially block from flowing in the opposite (retrograde) direction. The inner and/or outer surfaces of each of anchor assembly 101 and strut frame 105 may be partially or fully covered by cuffs or skirts, including those of fabric and/or tissue materials. An exemplary outer fabric skirt is shown on valve 100 in FIG. 1C.

Replacement heart valve 100 includes a delivery device attachment mechanism. For example, at least one atrial tip 114 of atrial anchor 102 forms crest 122 having attachment members 118, such as tines or pins, to which suture loops can be secured, shown in FIGS. 2A and 2B. In some embodiments, replacement heart valve 100 includes a plurality of attachment members 118. These attachment members 118 can be straight hooks, curved hooks, pins, tines, or other structures extending from a strut or member of the valve and to which a suture loop can be securely connected during shipment and subsequent delivery of the valve during implantation of the replacement heart valve 100. Attachment members 118 are sized and shaped to allow release of the suture loops from the attachment members and thus the valve after deployment of the valve within the patient. Thus, in the illustrated embodiment of FIG. 2B, attachment member 118 is in the form of a pin provided at the apex of each crest 122, with a free end extending toward the ventricular or outflow end of the replacement heart valve 100. Other exemplary structures that may be suitable for use as attachment member 118 are described in greater detail in U.S. Provisional Patent Application No. 63/171,148, filed Apr. 6, 2021 and titled "Frame Features for Transcatheter Mitral Valve Replacement Device," the disclosure of which is hereby incorporated by reference herein.

Figure 3A:
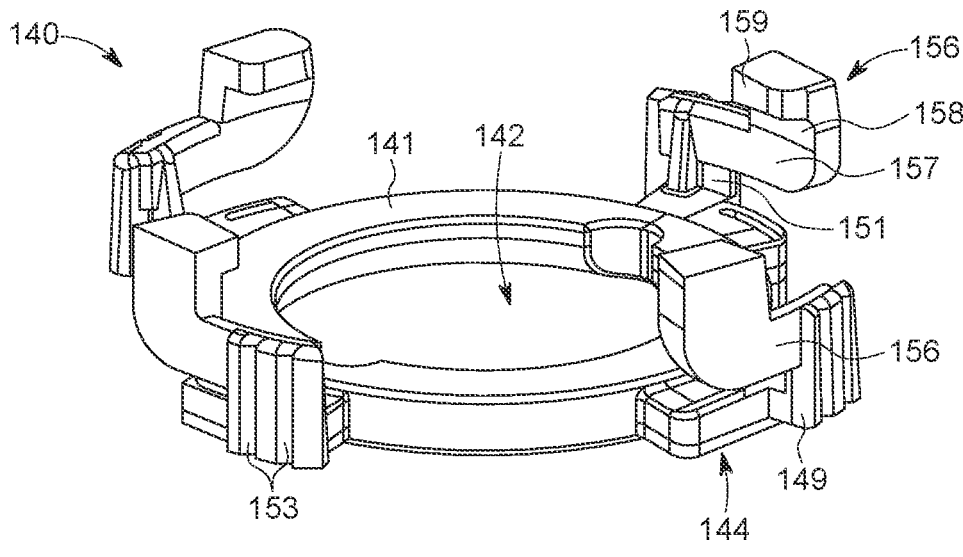
FIGS. 3A-3C are perspective, top and front views, respectively, of the ring of the packaging assembly of FIG. 1A.
Figure 3B:
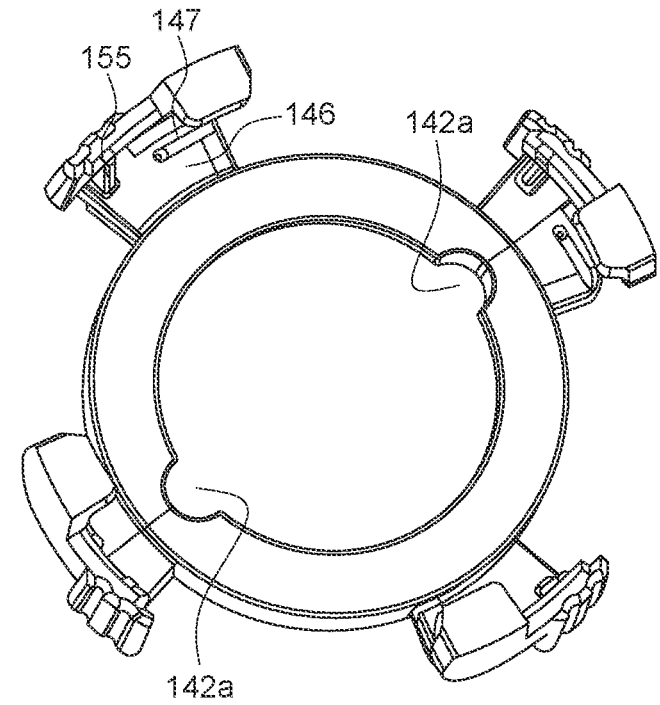

Ring 140 is described in further detail with reference to FIGS. 3A-3D. Ring 140 includes body 141 having an annular or circular shape and defining opening 142 therethrough. The opening 142 can define a plurality (e.g., a pair) of oppositely arranged cutouts 142a. In one example, the cutouts can be semi-circular and can be configured to prevent pinching of the heart valve during assembly. Ring 140 removably attaches to valve support 160 with an attachment mechanism. In the illustrated embodiment, the attachment mechanism is in the form of four spaced apart locking tabs 144 extending radially outward from body 141 and spaced around the circumference of the ring. As in the illustrated embodiment, locking tabs 144 may be evenly spaced apart around the circumference of body 141. Locking tabs 144 may be spaced about 90 degrees from adjacent locking tabs, as shown in FIG. 3B. In other examples, the locking tabs may be arranged at different intervals around body 141 relative to one another. In FIGS. 3A and 3B, ring 140 includes four locking tabs 144, although in other examples there may be more or fewer locking tabs.

Figure 3C:
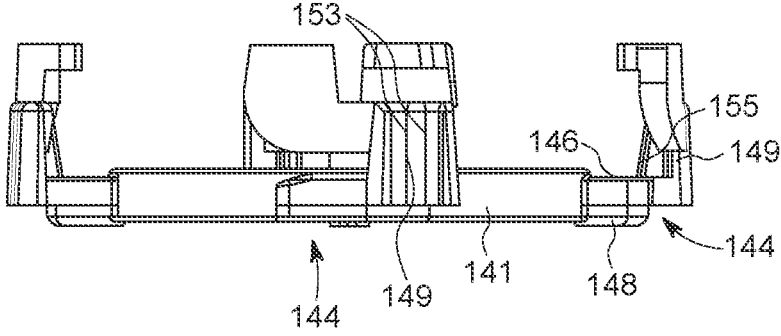
Figure 3D:
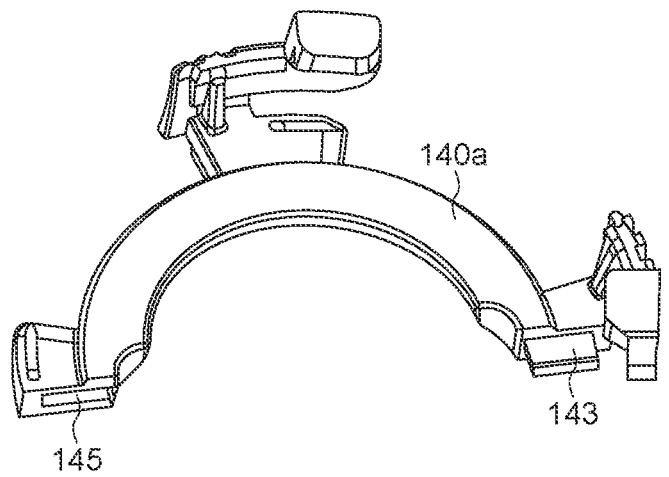
FIG. 3D is a perspective view of a first ring portion of the ring of FIG. 3A.

As shown in FIG. 3C, each locking tab 144 includes a proximal surface 146 and opposing distal surface 148. Proximal and distal surfaces 146, 148 may be substantially planar. Locking tab 144 includes primary extension 149 that extends the furthest radially outward of the locking tab 144. Primary extension 149 has a generally rectangular shape with the length extending in the proximal-distal direction, as best shown in FIG. 3C. Although, in other examples the primary extensions may be trapezoidal, round, triangular and are not limited to the shape shown in the figures. Primary extension 149 may also include ridges 153 on an outer surface thereof. In the illustrated embodiment, ridges 153 extend in the proximal-distal direction and may facilitate a user in readily gripping primary extensions 149 to manipulate (e.g. rotate) ring 140. It should be understood that additional or alternative texturizations may be provided to assist with manipulation and/or gripping of portions of ring 140. A ramp 155 may be positioned between primary extension 149 and body 141, and in the illustrated embodiment is connected to inner surface 151 (FIG. 3A) of primary extension 149 and proximal surface 146 to provide structural support for extension 149. Ramp 155 has a substantially triangular shape as shown in FIGS. 3A and 3C, which provides support to primary extension 149. Proximal surface 146 also includes a groove 147 shown in FIG. 3B for receiving a corresponding projection 179 (FIG. 4D) of the valve support to form a snap fit connection with the valve support, described in greater detail below.

Locking tabs 144 may allow ring 140 to be moved via rotation from an unlocked position to a locked position in which ring 140 is rotationally and axially locked with valve support 160. Such connection is described in further detail below in connection with additional descriptions of FIGS. 6A-6C. Primary extensions 149 may provide a hard stop feature to prevent over-rotation of ring 140 within valve support 160. Coupled to primary extensions 149 are secondary extensions 156, which include elongate portion 157 extending in a direction generally parallel to the circumference of body 141, perpendicular portion 158 extending in a proximal direction perpendicular to the elongate portion such that the elongate and perpendicular portions generally form an L-shape, and overhang 159 extending inwardly from the perpendicular portion. Secondary extensions 156 allow for the secure coupling of ring 140 to funnel 190, as is described below in greater detail.

Ring 140 may be modular, made up of two half pieces, first ring portion 140a and second ring portion 140b, which may be adapted to mate with each other to form ring 140. Each ring portion 140a, 140b includes male protrusion 143 extending from body 141 and locking tab 144 on a first end of the ring portion and a corresponding female aperture 145 defined by the body and locking tab on the opposing end of the ring portion, as shown on first ring portion 140a in FIG. 3D. Protrusion 143 and aperture 145 of first ring portion 140a are positioned opposite those of second ring portion 140b, such that the protrusion of the first ring portion mates with the aperture of the second ring portion, and the protrusion of the second ring portion mates with the aperture of the first ring portion to securely, but detachably, couple the ring portions to one another to form ring 140. Each ring portion 140a, b can also define a portion (e.g., half of a semicircle) of each of the cutouts 142a such that, when ring portions 140a,b are mated, the portions align to form the cutouts 142a. It is contemplated that ring 140 may be formed into any number of modular pieces (or otherwise a single non-modular piece) that may be attached to each other in the manner described above to form a full ring, such as 3 portions, 4 portions, etc.

Figure 4A:
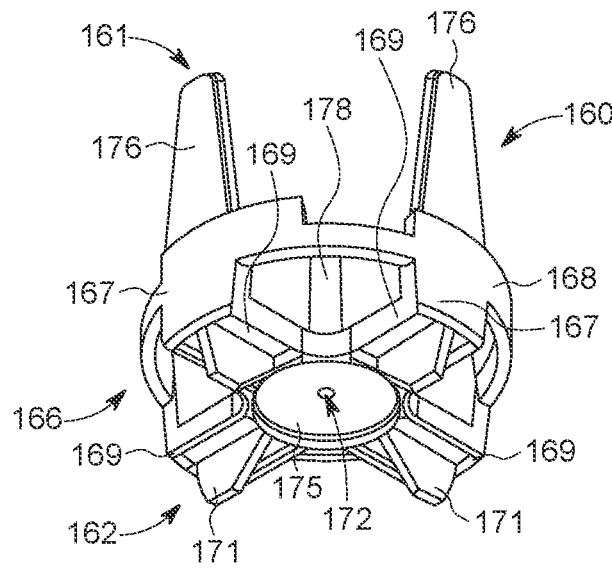
FIGS. 4A-4C are perspective, bottom, and front views, respectively, of the valve support of the packaging assembly of FIG. 1A.
Figure 4B:
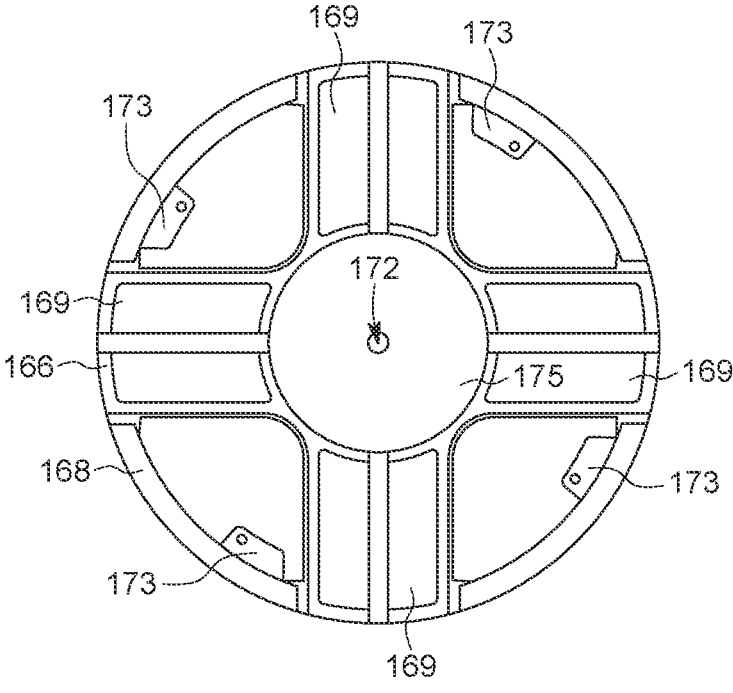

Valve support 160 is described in further detail with reference to FIGS. 4A-4D. Valve support 160 has proximal end 161 and distal end 162 and includes base 166 near the distal end. Base 166 includes outer rim 168 with four platforms 169 extending distally from rim 168 and connected to the rim by a respective arm 167, platforms which extend across rim 168 to form a "x'- or "cross"-shape such that outer rim 168 is radially outward of platforms 169, as shown in FIGS. 4A and 4B. A proximal surface of base 166 may include ridges along the surface to provide rigidity to the base. Platforms 169 connect to each other at central portion 175. The central portion 175 may be generally circular and may define a central opening 172 for receiving a pin 182 (shown in FIG. 6C) and/or a guidewire or other alignment tool therethrough. Each platform 169 may have a respective rib 171 extending distally from a distal surface of base 166, and ribs 171 may be positioned on respective platforms 169 between the outer diameter of the base and central portion 175. Ribs 171 may provide locations for the user to grasp valve support 160 to lift the valve support out of the jar, for example without sacrificing sterility of the replacement heart valve or contacting more sensitive components.

Figure 4C:
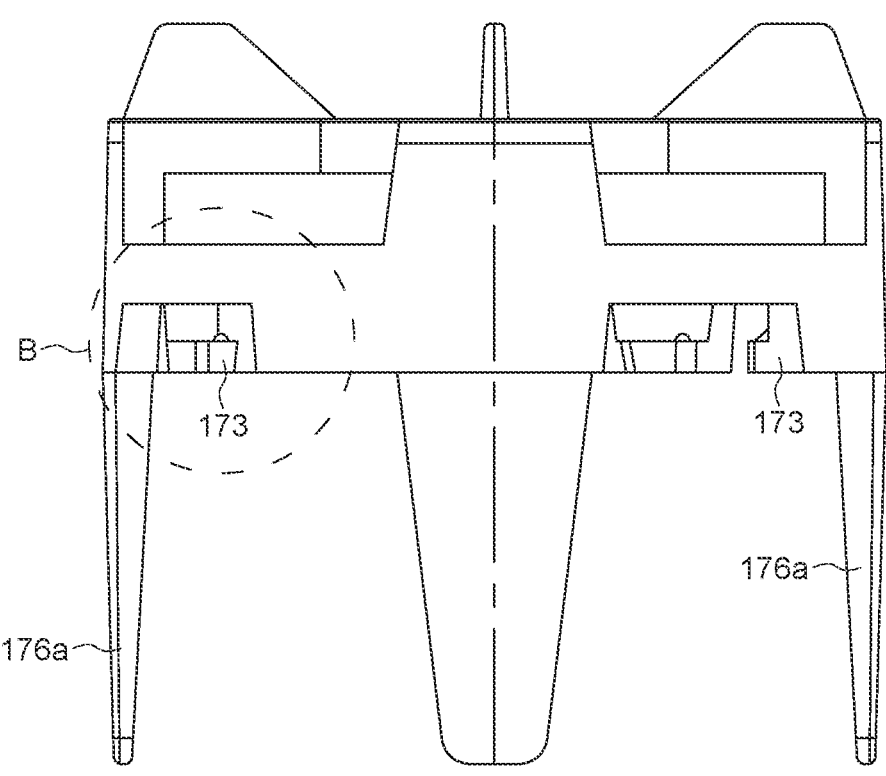
Figure 4D:
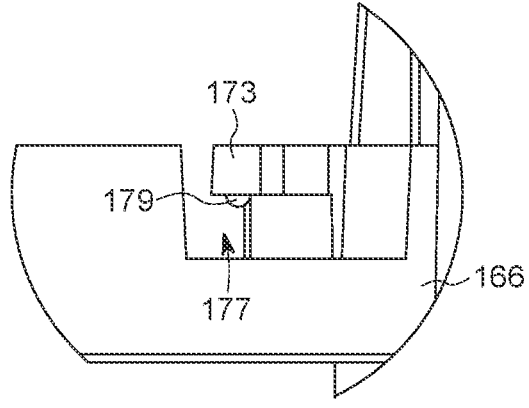
FIG. 4D is an enlarged view of a portion of the valve support of FIG. 4A.

Base 166 includes a plurality of fins 176 extending proximally from outer rim 168 which align with a respective one of the plurality of arms 167. Each fin 176 includes lateral side walls which taper inward in the proximal-distal direction such that the fin has a generally trapezoidal shape. Fins 176 are designed to provide rigidity to valve support 160 and protect replacement heart valve 100 from the walls of the jar or container during shipment. In this regard, fins 176 may be any shape including round, rectangular, triangular, which would enable the fins to provide rigidity to the structure. In this embodiment, there are four fins 176 equally spaced around the circumference of outer rim 168 of valve support 160 with the fins being spaced about 90 degrees apart from adjacent fins. Accordingly, the four arms 167 are also spaced apart from adjacent arms about 90 degrees. As shown in FIG. 4C, adjacent a side wall 176a of each fin 176 is ledge 173 projecting radially inward of outer rim 168 to define groove 177 between the ledge and outer rim for receiving a portion of locking tab 144. Further, ledge 173 includes projection 179 sized and shaped to engage groove 146 of locking tab 144 to form a snap fit connection. This connection rotationally and axially locks ring 140 to valve support 160. Ledge 173 and groove 177 are best shown in FIG. 4C and 4D. When locking tab 144 of ring 140 is positioned within groove 177 of valve support 160, extension 149 may abut a side surface of ledge 173 to prevent further rotation of ring 140, as shown in FIG. 6B.

With reference to FIG. 4A, valve support 160 further includes cannulated rod 178 defining a central lumen (not shown) which aligns with central opening 172 of central portion 175 of base 166, the lumen configured to receive pin 182 of retention mechanism 180. When replacement heart valve 100 is packaged within packaging assembly 50, cannulated rod 178 is positioned extending through central opening 106 of the replacement heart valve, and also through an opening between the prosthetic leaflets disposed within support frame 105. Rod 178 has an exterior surface that is advantageously smooth to prevent abrasion or damage to the replacement heart valve, including abrasion to the prosthetic leaflets.

Figure 5:
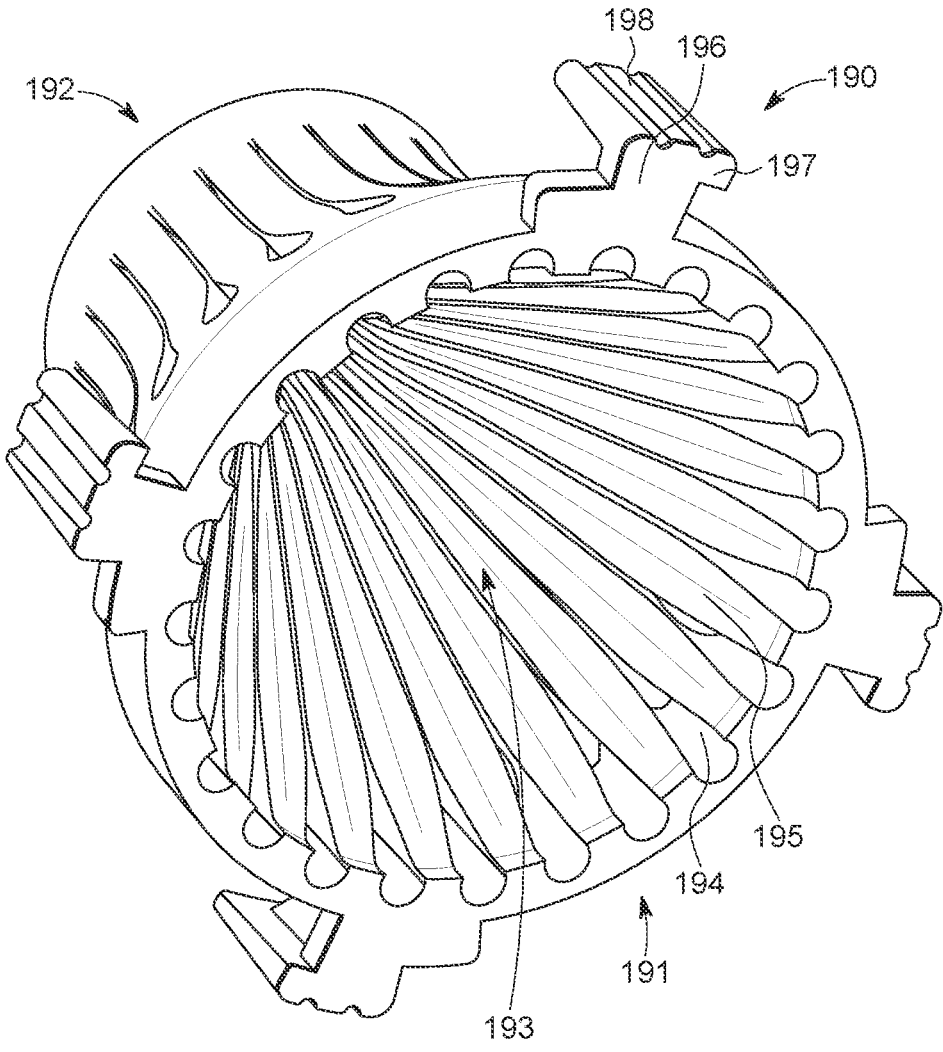
FIG. 5 is a perspective view of a funnel of the packaging assembly of FIG. 1A.

Funnel 190 is described in further detail with reference to FIG. 5. Funnel 190 defines a length extending from entry end 191 to exit end 192, wherein the entry end is nearer distal end 109 and the exit end is nearer proximal end 108 of packaging assembly 50 when in the fully assembled configuration. Funnel 190 defines lumen 193 therethrough, the lumen having a tapering diameter corresponding to an inner surface of the funnel. That is, lumen 193 may have the same diameter as the inner surface of funnel 190 along any plane extending perpendicular to a longitudinal axis along which the funnel extends. When funnel 190 is used as intended, a replacement valve, such as valve 100, may be translated through the funnel in a loading direction, entering the funnel at entry end 191 and emerging from the funnel at exit end 192. Funnel 190 has a first diameter at entry end 191 and a second diameter at exit end 192, the second diameter being smaller than the first diameter. The diameter of funnel 190 may taper as the funnel extends from entry end 191 to exit end 192. In some examples, the rate at which the diameter of funnel 190 tapers may vary such that the diameter tapers more rapidly near entry end 191 than it tapers near exit end 192. In other examples, the rate at which the diameter tapers may be consistent for the full length of the funnel. The second diameter at exit end 192 may be equal to or smaller than the interior diameter of a component of a delivery device such that valve 100 may be translated through funnel 190 in the loading direction and transition smoothly from the funnel into the delivery device. In other words, when valve 100 is translated through funnel 190 from entry end 191 to exit end 192, the valve may substantially abut the interior surface of the funnel, and the relative sizing of the exit end of the funnel and the opening of the delivery device receiving the valve may allow the valve to transition smoothly into the delivery device, the valve collapsing as it translates through the funnel.

Funnel 190 includes slots 194 extending along a length of the funnel. Funnel 190 has a wall thickness, and slots 194 may extend through the entire wall thickness of the funnel as illustrated in FIG. 5, or alternatively through part of the wall thickness of the funnel, so long as the slots are sufficiently deep that the free ends of the tines 107 of valve 100 do not contact and/or scrape the interior of the funnel as the valve translates through the funnel, as described further below. Funnel 190 includes a plurality of slots 194 disposed along a length of the funnel and spaced approximately equal distances apart from one another. In some examples, funnel 190 may include 24 slots and valve 100 may include 24 tines 107. Each slot 194 is a long and narrow partial or complete void defined by funnel 190 configured to receive a corresponding tine 107 of valve 100. Each slot 194 extends from the circumference of exit end 192 of funnel 190 to a circumferential axis near (but preferably spaced apart from) the circumference of entry end 191 of the funnel. In other words, slots 194 may not extend up to and through entry end 191 of funnel 190, but may stop short before reaching the entry end, leaving a portion of the funnel as a solid continuous portion around the circumference at the entry end. Slots 194 may extend up to and through exit end 192, but need not extend through the entire thickness of funnel 190 at the exit end, leaving a continuous portion of the circumference at the exit end similar to that of entry end 191. It is also contemplated that slots 194 may extend through the entire thickness of funnel 190 up to and through exit end 192. Slots 194 have a first width near entry end 191 and a second width near exit end 192, the first width larger than the second width. The width of slots 194 tapers as the slots extend along the length of the funnel 190 from entry end 191 to exit end 192 to allow for self-alignment of replacement valve 100 by guiding tines 107 in place as the valve translates through the funnel and maintains the radial alignment of the valve. Funnel 190 further includes grooves 195 which further contribute to maintaining the alignment of valve 100. For example, stent cells of the atrial and/or ventricular anchors 102, 104 may be disposed at least partially within grooves 195 as valve 100 translates through funnel 190, which may serve as an additional measure for preventing the valve from rotating out of alignment. In other examples, the partial grooves 195 may be omitted and the region between slots 194 can be any type of shape, such as flats, bumps, semi-circular grooves, V-shaped, etc.

As noted above and shown in FIG. 2A, valve 100 includes tines 107 extending generally radially outward from anchor assembly 101 of the valve. Tines 107 are spaced approximately equal distances apart around the outer circumference of anchor assembly 101, which distance may correspond to (e.g., be equal to) the spacing between adjacent slots 194, at least near the entry end 191 of the funnel. Tines 107 have generally traumatic tips that have the potential to scrape along the interior surface of funnel 190 as valve 100 translates through the funnel. To accommodate for the traumatic tips of tines 107, each tine may align with a slot 194 of funnel 190. As valve 100 translates through funnel 190, each tine 107 may protrude into and/or through a corresponding slot 194, while the funnel may contact other portions of the valve and apply an inward force against the surface area of the valve surrounding the tines. In other words, valve 100 may be gradually compressed as it is translated through funnel 190 while tines 107 (and particularly the traumatic free ends of the tines) generally do not contact any solid surface of the funnel. Such an arrangement may help to avoid scraping of tines 107 against funnel 190 which might otherwise lead to particulate generation and/or wear of both the tines and the funnel. Further, the evenly spaced structure of tines 107 and the corresponding evenly spaced structure of slots 194 may promote an even or uniform collapse of valve 100 by forcing radial symmetry of the valve as the valve translates through the funnel and the narrowing internal diameter of the funnel collapses the valve 100. That is, the nature of passing tines 107 through slots 194 maintains equal positioning of the tines with respect to each other as valve 100 is collapsed, causing a uniform collapse of the valve. This uniform collapse may be further supported via the interaction of stent cells with grooves 195.

Securement members 196 extend radially outward from the circumference of funnel 190 at entry end 191. Funnel 190 includes four securement members 196 spaced approximately 90 degrees apart from one another along the circumference, but any number of securement members spaced any distance apart is contemplated. Securement members 196 are similar to locking tabs 144 of ring 140 described above, the securement members adapted to secure funnel 190 to either ring 140 or valve support 160. That is, securement members 196 include a lip 197 along the radially outermost portion of the securement members which includes a groove (not shown) on the proximal face of the securement members substantially similar to groove 147 on locking tab 144. Thus, in examples of packaging assembly 50 excluding ring 140, funnel 190 may be coupled and locked to valve support 160 in the same or substantially the same manner as the ring is coupled to the valve support above, wherein protrusions 179 of the valve support engage the grooves on the securement members in the locked configuration. It should be noted that overhang 159 of secondary extension 156 on ring 140 includes a protrusion (not shown) substantially similar to protrusion 179, and thus in examples of packaging assembly 50 including the ring, the ring may be coupled to valve support 160 in the manner described above, and funnel 190 may be coupled to the ring in substantially the same manner with the protrusions of the overhangs of the ring engaging the grooves of the securement members in the locked configuration. In other words, the similarity in structure of the connection mechanisms of valve support 160, ring 140 and funnel 190 allows the funnel to be interchangeably coupled either directly to the valve support or to the ring which is coupled to the valve support. For purposes of clarity, in examples such as the embodiment shown in FIG. 1A, packaging assembly 50 may be referred to as being in a locked configuration when ring 140 is coupled to valve support 160, and funnel 190 is coupled to the ring. Packaging assembly 50 may further be referred to as being in a partially locked configuration when two of the above components are coupled to each other, but the third component is not coupled to the other two, e.g., valve support 160 is coupled to ring 140 while ring is not coupled to funnel 190, or the funnel is coupled to the ring while the ring is not coupled to the valve support. Still further, packaging assembly 50 may be referred to as being in an unlocked configuration when none of valve support 160, ring 140 nor funnel 190 are coupled to one another. Similar to locking tabs 144, a radially outermost surface of securement members 196 includes ridges 198 which may facilitate a user in readily gripping the securement members to manipulate (e.g. rotating) funnel 190. It should be understood that additional or alternative texturizations may be provided to assist with manipulation and/or gripping of portions of funnel 190.

Figure 6A:
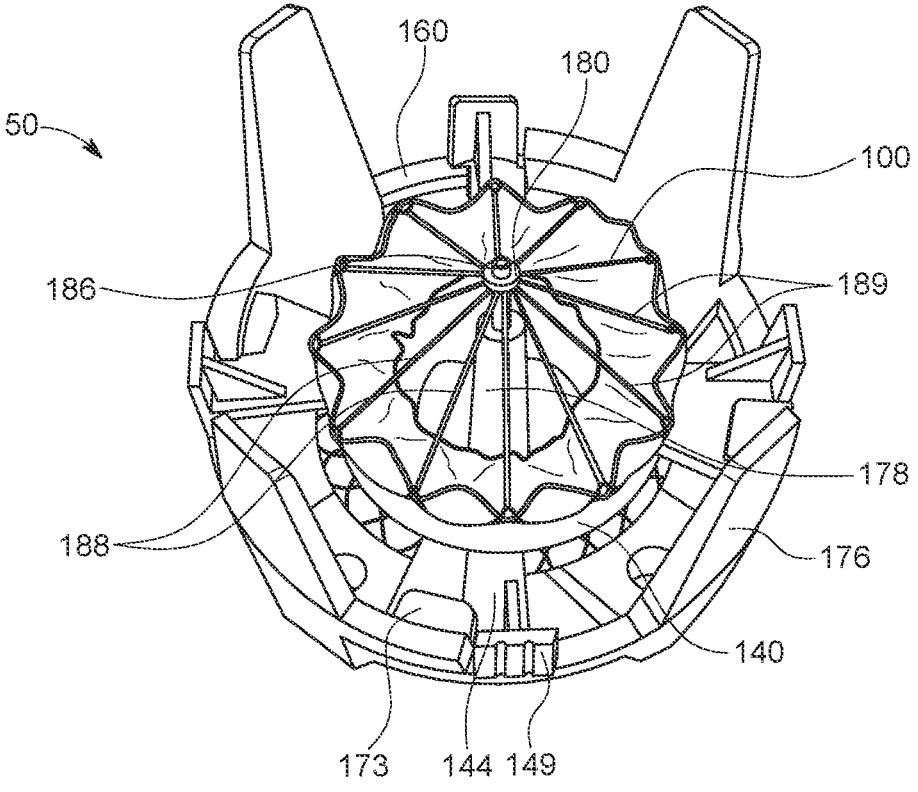
FIGS. 6A-6B are perspective and front views, respectively of the packaging assembly of FIG. 1A without a funnel.
Figure 6B:
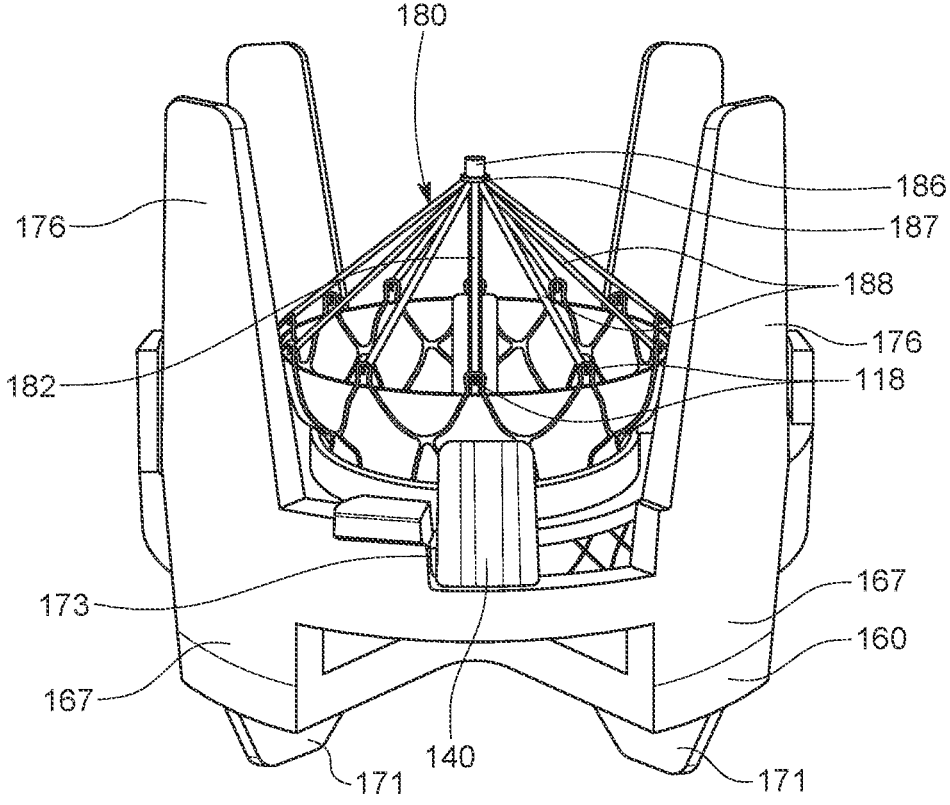
Figure 6C:
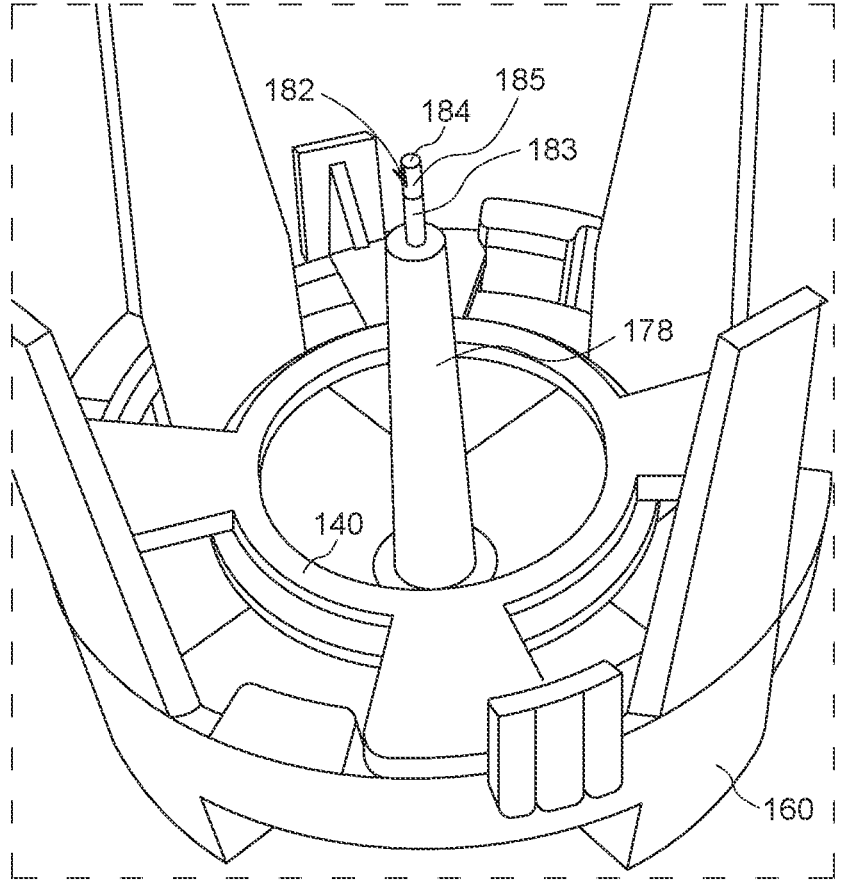
FIG. 6C is a perspective view of the packaging assembly of FIG. 6A without a cap, collar, and sutures of a retention mechanism and without a frame of the prosthetic heart valve.

FIGS. 6A-6C show packaging assembly 50 according to an aspect of the present disclosure in a partially assembled configuration. It should be noted that packaging assembly 50 is shown in FIGS. 6A-6C without a funnel 190 and without secondary extensions 156 coupled to primary extensions 149 of ring 140, and also shown in FIG. 6C without replacement heart valve 100, but otherwise includes the same structure as the embodiment described above. In this regard, packaging assembly 50 is designed for use in conjunction with replacement heart valve 100 to form a system for heart valve replacement. Packaging assembly 50 includes ring 140 coupled to and positioned at least partially within valve support 160, as shown in FIGS. 6A and 6B. Ring 140 and valve support 160 may each be formed via injection molding, although other manufacturing methods may be suitable. Packaging assembly 50 further includes retention mechanism 180 (described further below) for securely attaching and tensioning replacement heart valve 100 so that the replacement heart valve is already prepared for attachment to the delivery device while in the packaging, allowing for more efficient implantation. Assembled ring 140 has an inner diameter sized such that the ring fits snugly around central portion 103 of replacement heart valve 100 to prevent the replacement heart valve from shifting when positioned in a final configuration in the packaging assembly 50. In some embodiments, the inner diameter of ring 140 is about equal to, slightly larger, or slightly smaller than, the exterior diameter of central portion 103 of replacement heart valve 100 while the replacement heart valve is in the expanded condition. Accordingly, ring 140 has an outer diameter that allows the ring to fit within the valve support.

Ring 140 may attach to valve support 160 with an attachment mechanism that allows the ring to removably attach to the valve support such that the ring and valve support can be moved from an unlocked configuration in which the two are detached and can rotate relative to one another to a locked configuration in which the ring is rotationally and axially locked to the valve support. Generally, valve support 160 forms the holding component of the packaging assembly 50 in which replacement heart valve 100 is securely positioned. Accordingly, valve support 160 defines an inner diameter that that allows the ring to fit within the valve support. Further, the height and outer diameter of valve support 160 are sized and configured to fit within a shipment jar or packaging container. With this sizing, valve support 160 does not interfere with the seal of the jar or container. Additionally, the size and shape of valve support 160 allows for easy insertion and removal of the valve support from the jar or container, such that sufficient clearance is provided to allow for insertion and removal of the valve support without damage to the valve support and/or replacement heart valve 100, while also partially or fully limiting motion of the valve support within the jar or container during transportation.

As shown in FIG. 6B, retention mechanism 180 of packaging assembly 50 includes pin 182, cap 186 for attaching to pin 182, and sutures (or other thread-like components) 188 for attaching the retention mechanism to replacement heart valve 100. A first end of each of sutures 188 is secured to cap 186 and a second end of each suture includes a loop to slip over and attach to attachment members 118 of replacement heart valve 100. Retention mechanism 180 allows for secure attachment of replacement heart valve 100 within packaging assembly 50 during shipment, removal from the shipment jar or container, rinsing of the replacement heart valve, and coupling to the delivery device.

As shown in FIG. 6C, cannulated pin 182 includes a distal portion 183 having a first diameter which transitions to a proximal portion 184 having a second diameter at step 185, the second diameter being smaller than the first diameter. Proximal portion 184 is sized and configured to fit within an inner lumen (not shown) of cap 186. Cap 186 can be attached to pin 182 via a cooperating threaded engagement between an external surface of proximal portion 184 and an inner surface of cap 186 (not shown) which defines the lumen.

Step 185 forms a shoulder to control the position of cap 186 on pin 182. The outer surface of cap 186 is threaded for attaching the delivery system to the retention mechanism 180 of packaging assembly 50. Cap 186 includes a portion, either monolithic with the cap or attached thereto, that enables sutures 188 to be threaded therethrough. In the illustrated embodiment, cap 186 includes collar 187 having a plurality of openings (not shown) for receiving suture strands 188 such that a first end of the suture can be secured through the openings thereby securing sutures 188 to the cap. Cap 186 and collar 187 may be monolithic, e.g. constructed from a single piece, or they may be separate pieces mechanically joined together thereafter. A second end of each suture 188 is looped over a respective one of the plurality of attachment members 118 on a proximal end of replacement heart valve 100, creating a connection between the valve and the pin. Sutures 188 may be tensioned, e.g., by maintaining replacement heart valve 100 at a distance relative to pin 182. In one example, there may be twelve suture strands 188 connected to pin 182 and attachment members 118. In order to achieve tension on suture strands 188, pin 182 is designed to have a height sufficient to create such tension when the suture strands are positioned through the retaining elements and cap 186. Pin 182 can be positioned within rod 178 to the desired height based on the size of the replacement heart valve. In order to maintain pin 182 within the lumen of rod 178, the pin is structured to facilitate an interference fit. In one example, pin 182 may be tapered such that the outer diameter of the pin at a particular location is greater than the inner diameter of rod 178 at a particular location. This enables pin 182 to be inserted to a specified depth and kept in place. Alternatively, pin 182 could include threads for threaded engagement with the internally threaded rod, or the pin and/or lumen of the rod could be stepped and the engagement could be achieved through a friction fit of the stepped configuration. Crimp members 189, such as knots, may be provided around at least a portion of each suture strand 188 to form the loop at the end of the suture. Crimp members 189 may also help to prevent possible hooking onto other features of the packaging assembly. In some cases, the crimps or coils on the sutures are secured in place by an adhesive, which can help maintain tension and avoid inadvertent separation of the sutures. Although described herein as suture, the material can alternatively be wire or another flexible member capable of tensioning the replacement heart valve 100.

Figure 7A:
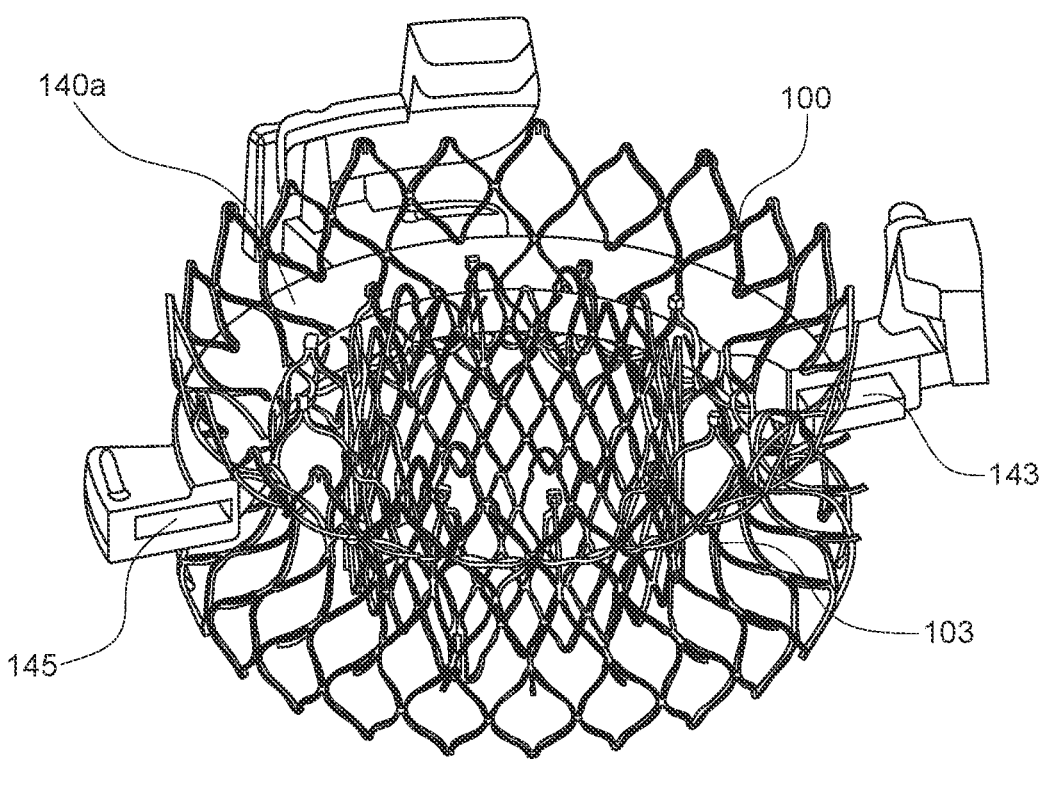
FIG. 7A is a perspective view of the replacement heart valve of FIG. 2A with a first ring portion positioned around the valve.
Figure 7B:
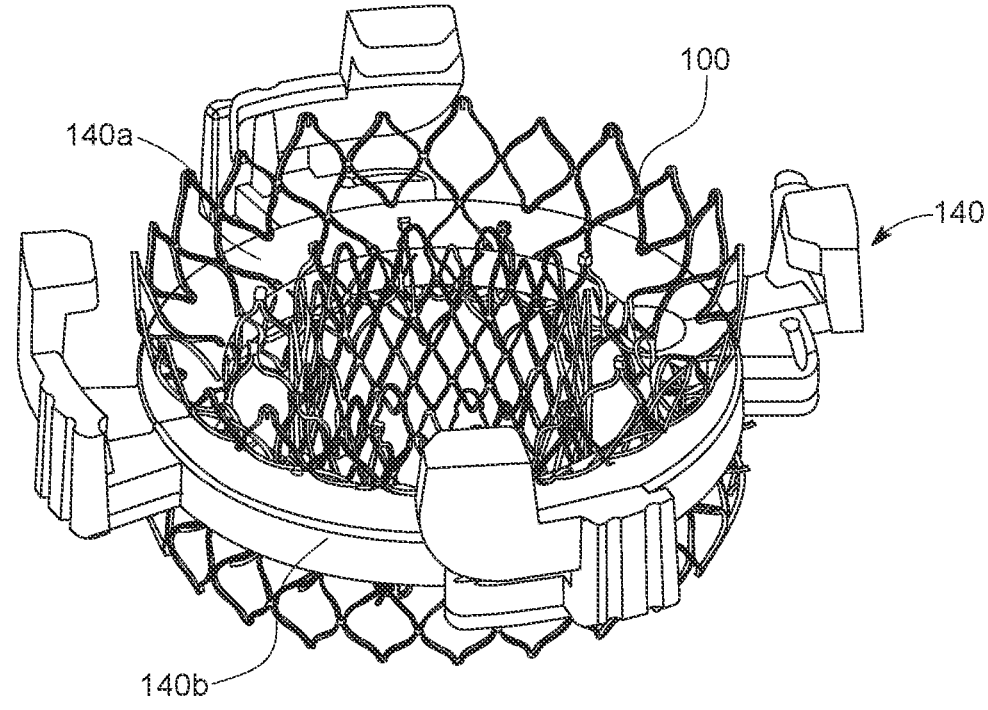
FIG. 7B is a perspective view of the replacement heart valve of FIG. 2A with a ring positioned around the valve.

Ring 140 may be assembled with valve 100, as shown in FIGS. 7A-7B. As described above, ring 140 may be modular such that it may be separated into two (or more) modular pieces, first ring portion 140a and second ring portion 140b, which may be detachably coupled to one another. First ring portion 140a may be positioned around anchor assembly 101 of valve 100 such that the first ring portion circumferentially surrounds about half of the central portion 103 of the valve as shown in FIG. 7A. Ring 140 may be sized such that the inner diameter of the ring (i.e., the distance between opposite points along the inner circumference of the ring) is substantially similar to the diameter of central portion 103 of valve 100 and smaller than the diameter of the valve at the atrial and ventricular anchors when the ring is assembled and the valve is mostly or fully expanded. Such relative sizing between ring 140 and valve 100 allows the ring to be nested within central portion 103 of the valve to securely hold the valve in place relative to the packaging assembly, thereby preventing undesired movement (including axial movement) of the valve when in the packaged configuration during shipping. Second ring portion 140b may be positioned around the remaining uncovered portion of central portion 103 of valve 100 in a manner substantially similar to that of first ring portion 140a, and protrusions 143 of each of first and second ring portions 140a, 140b mate with the corresponding apertures 145 of the other ring portion to detachably couple the first and second ring portions together to form assembled ring 140. This configuration may allow for the ring 140 to surround the valve 100 without having to crimp the valve and pull the valve through the open center of the ring, which might otherwise be required if the ring were formed as a single monolithic piece.

As noted above, packaging assembly 50 is shown in a partially assembled configuration in FIGS. 6A-6C, in which ring 140 and valve support 160 are locked together and replacement heart valve 100 is positioned within and secured to ring 140, the ring is positioned within valve support 160 and rotated in a first direction such that locking tabs 144 slide into the grooves defined by ledges 173 and mechanically lock to valve support 160 via the snap fit connection. Pin 182 is positioned within a proximal portion of cannulated rod 178 with proximal portion 184 of the pin extending beyond the rod. Body 141 of ring 140 is positioned so that it securely fits around the waist defined by central portion 103 of the hour-glass shaped anchor assembly 101 of replacement heart valve 100. Replacement heart valve 100 is positioned with ventricular anchor 104 adjacent base 166 of valve support 160. This allows for a circumferentially snug and secure fit which reduces and/or prevents movement of replacement heart valve 100 within packaging assembly 50. Pin 182 extends coaxial with a longitudinal axis of replacement heart valve 100. Cap 186 is attached to pin 182 with suture strands 188 looped through the openings of cap 186. For ease of assembly, suture strands 188 can be looped through the openings of cap 186 prior to attachment of the cap with valve support 160 and ring 140 structure. The loops of suture strands 188 are attached to attachment members 118 of atrial anchor 102 of replacement heart valve 100 thereby tensioning suture strands 188. The tension on suture strands 188 prevents inadvertent release of the suture loops on attachment members 118 (e.g. by preventing the suture loops from slipping off the pins of the attachment members 118). The tension on the suture strands 188, in combination with ring 140 limiting axial movement of the prosthetic valve 100, also constrains the valve fully in the axial direction. Further, the tension of suture strands 188 also holds cap 186 against the shoulder of pin 182. Thus, the positioning of body 141 of ring 140 around the valve together with the tension of suture strands 188 provides for full axial and circumferential securement of replacement heart valve 100. In the process of loading valve 100 into a delivery device, once the valve is connected to the delivery device, the tension is transferred from ring 140 to the delivery device, and the ring no longer serves a function and may thus be disassembled by separating first ring portion 140*a* from second ring portion 140*b* to remove the ring from the assembly altogether.

Figure 8A:
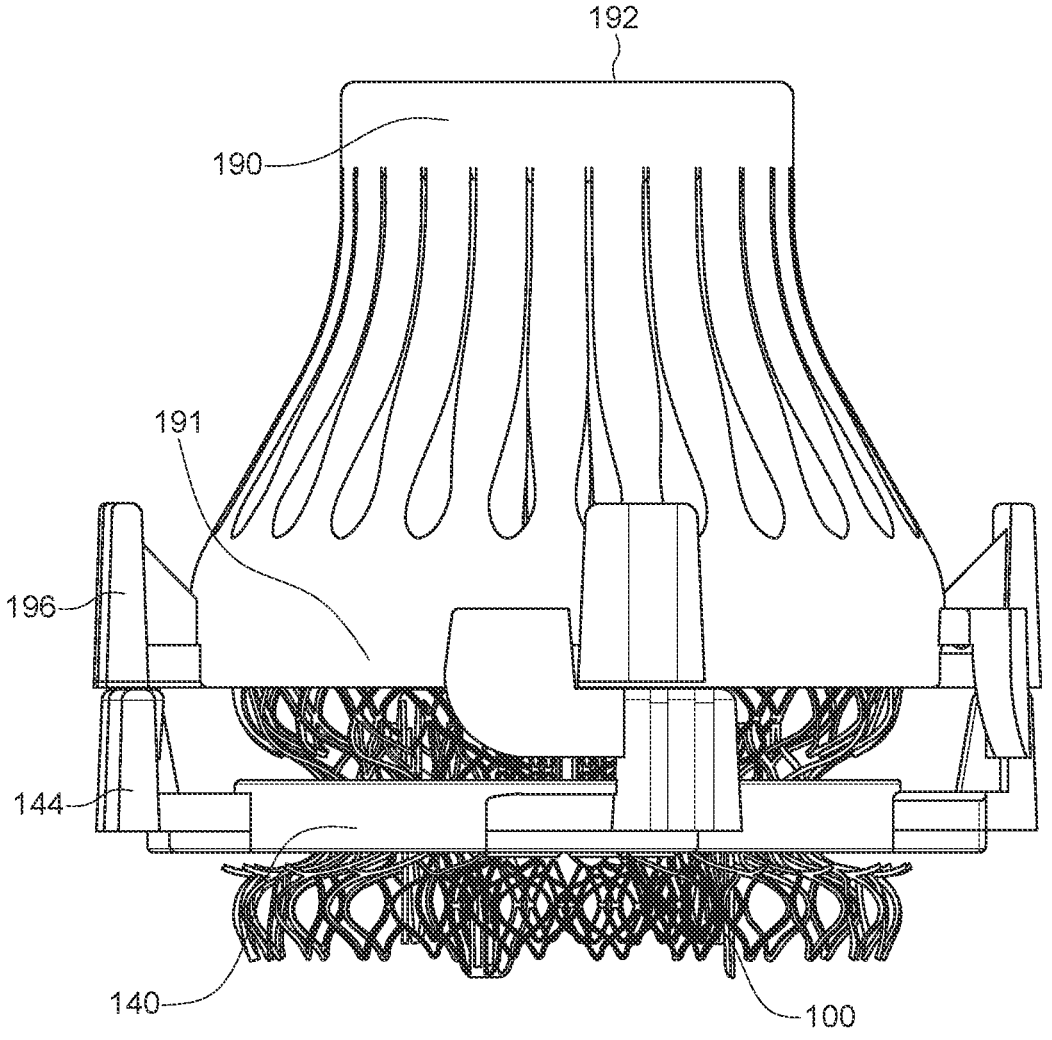
FIG. 8A-8B are front and top views, respectively, of the packaging assembly of FIG. 1A without a valve support.

An assembled ring 140 surrounding valve 100 is shown in FIG. 8A with funnel 190 coupled to the ring. Funnel 190 is oriented with entry end 191 adjacent ring 140. Each securement member 196 on funnel 190 is coupled to a corresponding locking tab 144 on ring 140. To couple securement members 196 to locking tabs 144, entry end 191 of funnel 190 may be positioned adjacent ring 140 such that a distal surface of the securement members (i.e., surface facing downward in FIG. 8A) abuts a proximal surface of the locking tabs (i.e., surface facing upward in FIG. 8A), and the funnel may then be rotated in a locking direction relative to the ring so that the lip 197 of each securement member engages with and slides under the overhang 159 of each locking tab, and a protrusion on the overhang engages with a groove on the lip as described above, inhibiting any relative rotational or axial movement between the funnel and the ring. The engagement between securement members 196 and locking tabs 144 may generally maintains the ring and funnel in their respective positions until a user manipulates the assembly to rotate the funnel in an opposite, unlocking direction relative to the ring to release the funnel from the locked position.

Figure 8B:
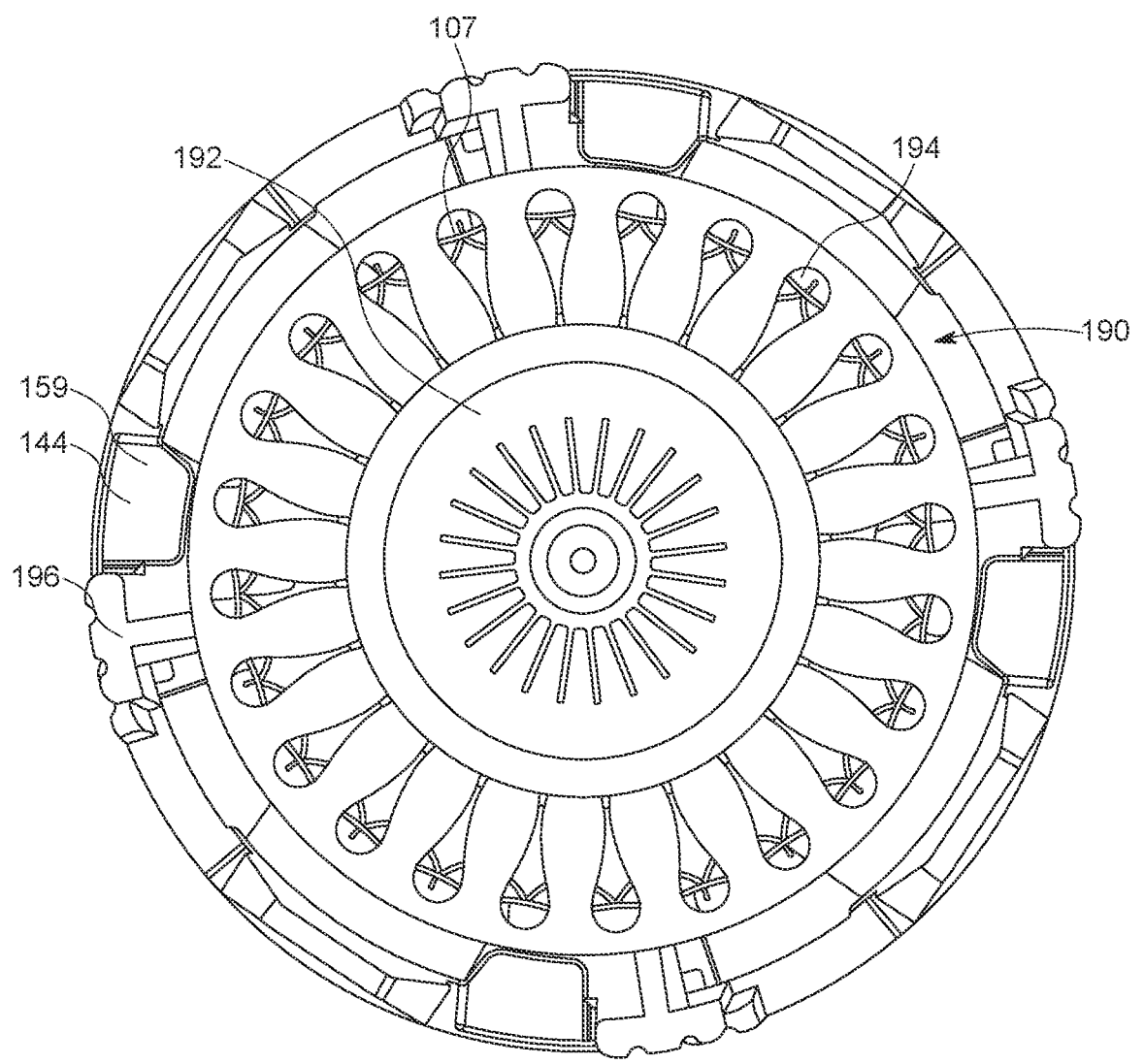

FIG. 8B illustrates a proximal end view of the assembly shown in FIG. 8A showing exit end 192 of funnel 190. Each locking tab 144 of ring 140 is shown engaged with a corresponding securement member 196 of funnel 190, in which lip 197 of each securement member is covered by overhang 159 the corresponding locking tab in the illustrated view. Further, each tine 107 of valve 100 is shown in alignment with a corresponding slot 194 of funnel 190 to encourage and maintain radial alignment of the valve relative to the funnel. Exit end 192 of funnel 190 may include a cylindrical indentation wherein the indented portion of the exit end has a first radius which is smaller than the radius of packaging assembly 50 overall. That is, exit end 192 includes a circumferential portion which is not indented and extends farther in the proximal direction than the cylindrically indented portion. The cylindrical indentation may be sized and shaped to receive delivery device 60, as shown in FIGS. 10E and 10F, so that the delivery device can securely engage with exit end 192 of funnel 190 and allow for a smooth transition of replacement heart valve 100 from the funnel to the delivery device. Further, it should be noted that each slot 194 shown in FIG. 8B on exit end 192 of funnel 190 may be a continuation of the corresponding slot extending along the side wall of the funnel, which allows tines 107 to be translated completely through the funnel without interruption.

Figure 9:
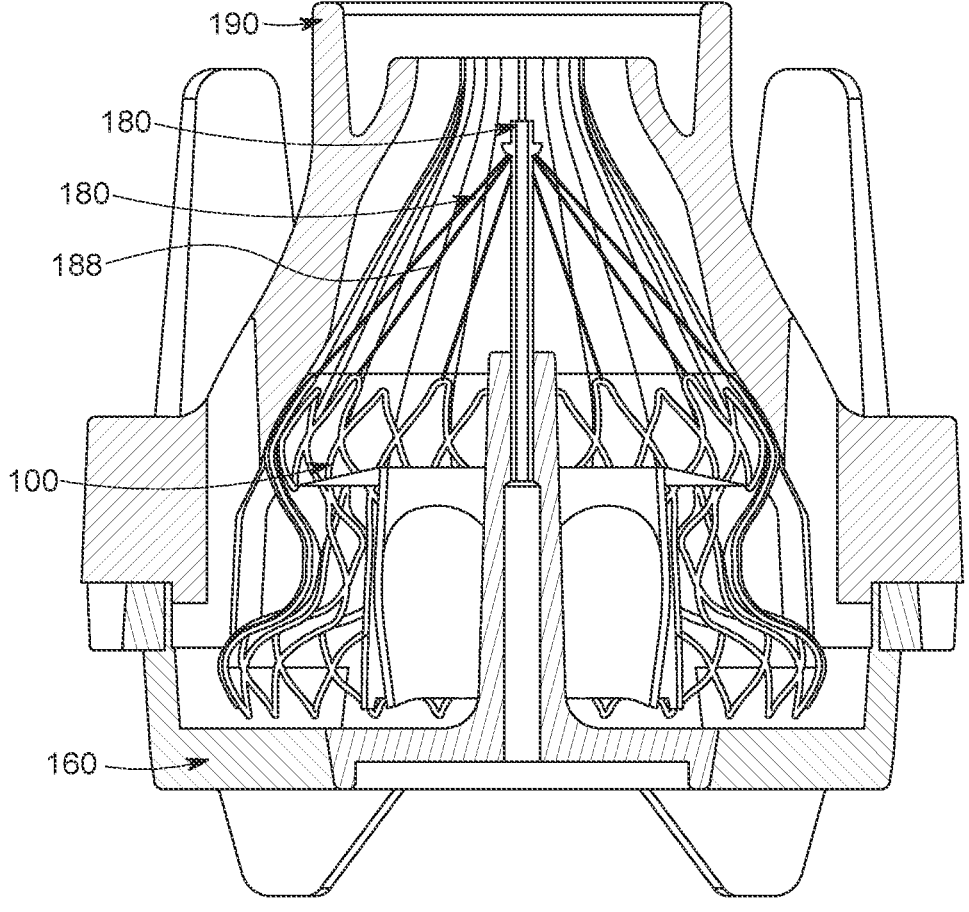
FIG. 9 is a front transparent view of the packaging assembly of FIG. 1A without a ring.

In some examples, as shown in FIG. 9, packaging assembly 50 need not include ring 140. The example of FIG. 9 includes valve support 160, valve 100 coupled to the valve support, and funnel 190 coupled directly to the valve support and positioned over the valve. In such an example, securement members 196 of funnel 190 couple to groove 177, ledge 173 and protrusion 179 of valve support 160 as described above. The inner surface of funnel 190 may apply a force to valve 100 resisting the force caused by the tension applied by sutures 188. In other words, sutures 188 may be coupled to attachment members 118 of valve 100, and the valve may abut the inner surface of funnel 190 to create and maintain the tension in the sutures. Thus, in the example without ring 140, valve 100 may remain under substantially the same forces applied by sutures 188 and funnel 190 to hold the valve securely in place within the packaging assembly during shipping.

Figure 10A:
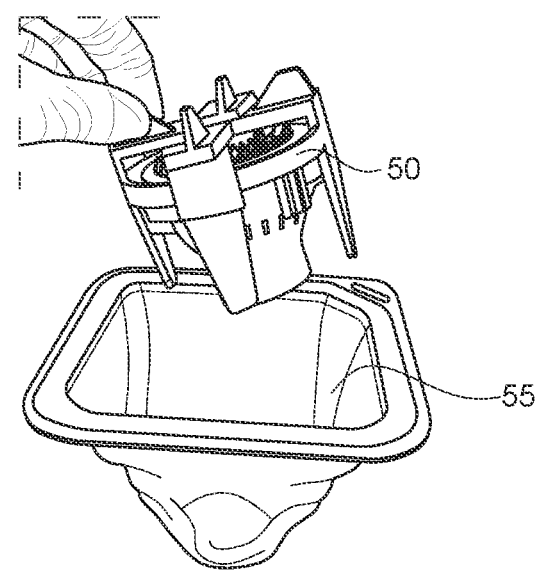
FIG. 10A-10O show various steps of removing the packaging assembly of FIG. 9 from packaging and transitioning the replacement heart valve from an expanded configuration to a collapsed configuration through the funnel and into a delivery device.
Figure 10B:
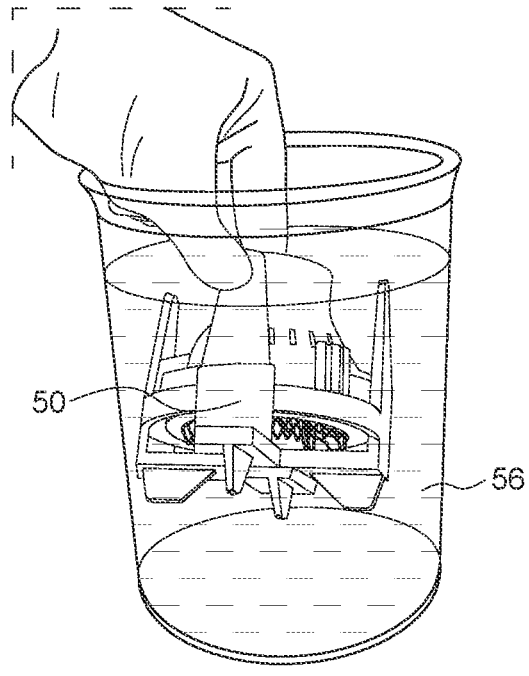
Figure 10C:
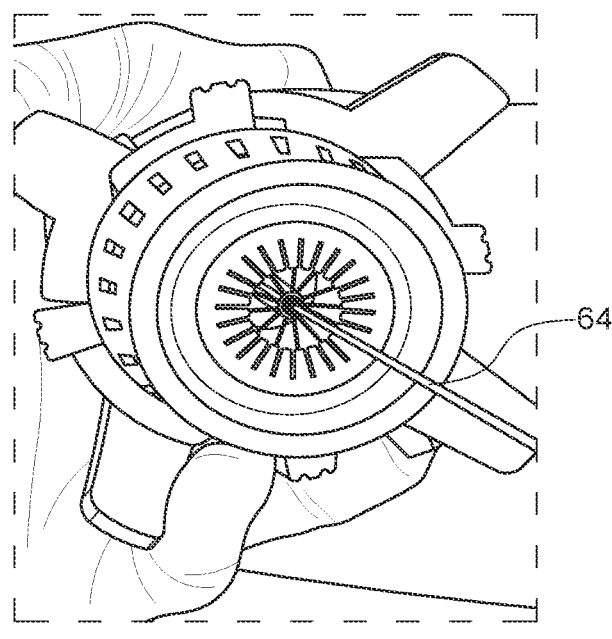
Figure 10D:
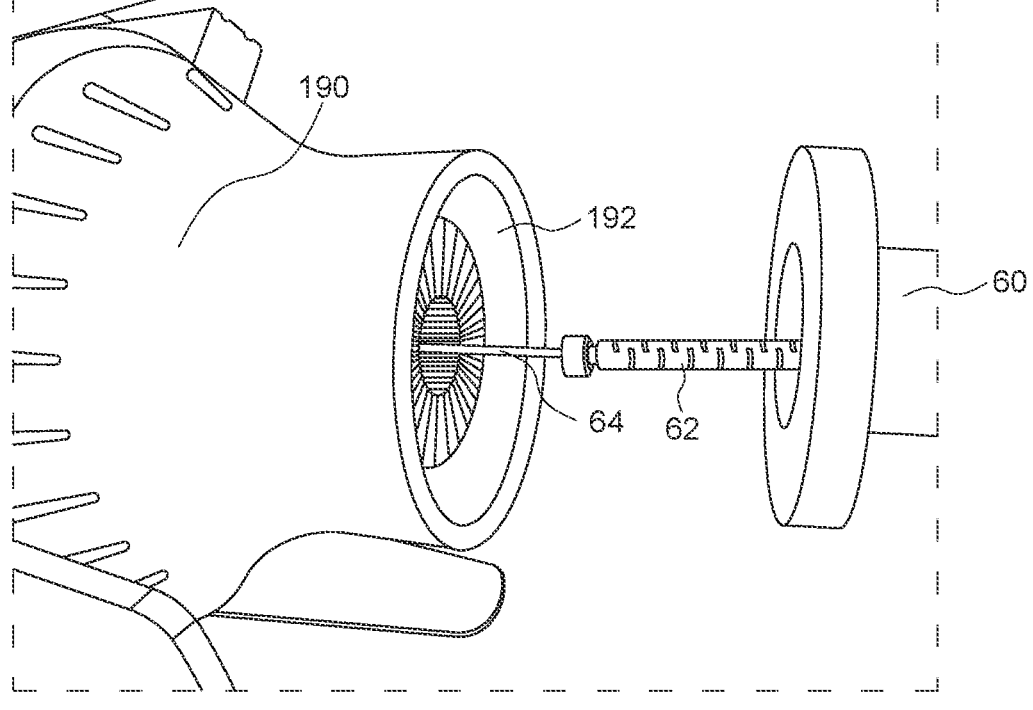
Figure 10E:
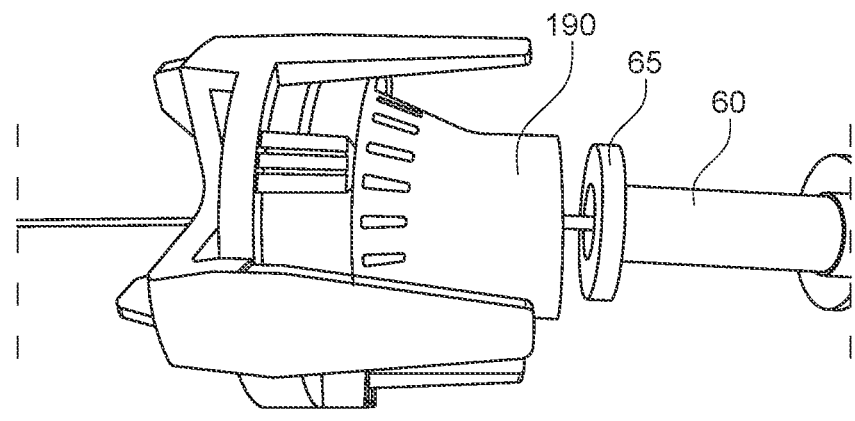
Figure 10F:
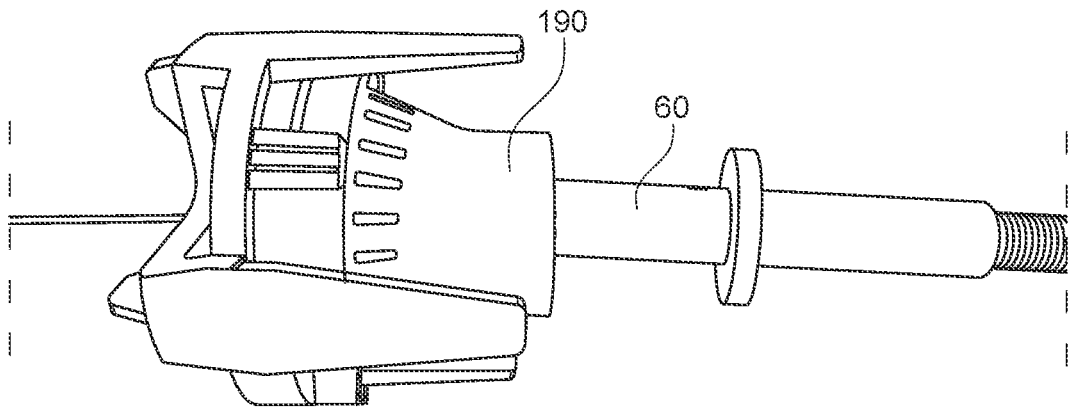
Figure 10G:
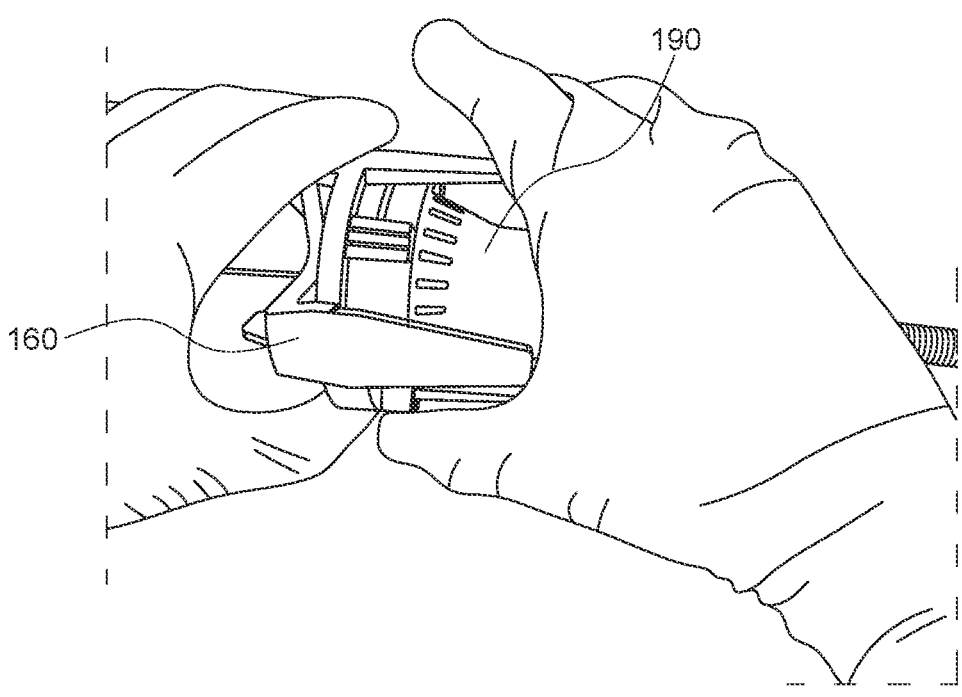
Figure 10H:
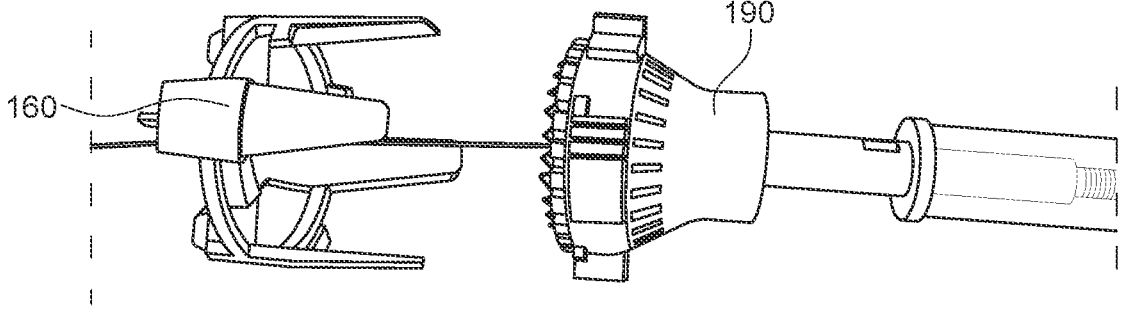
Figure 10I:
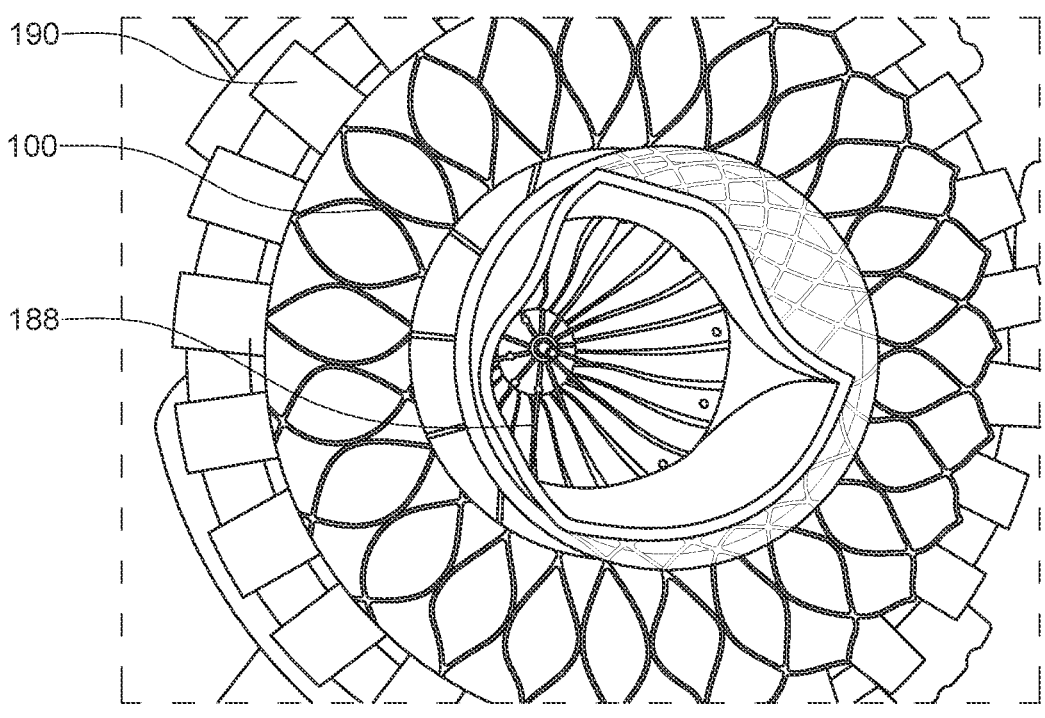
Figure 10J:
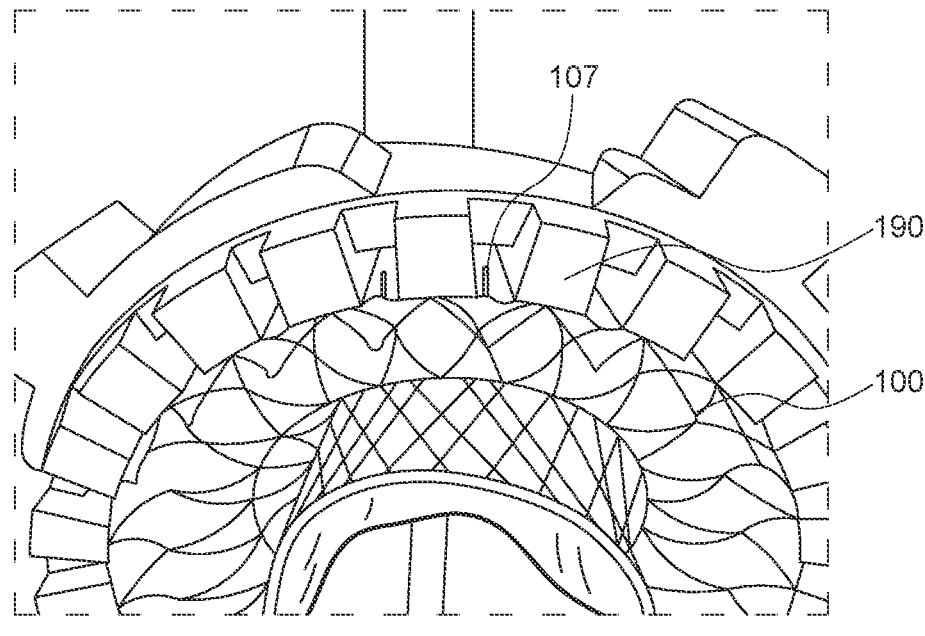
Figure 10K:
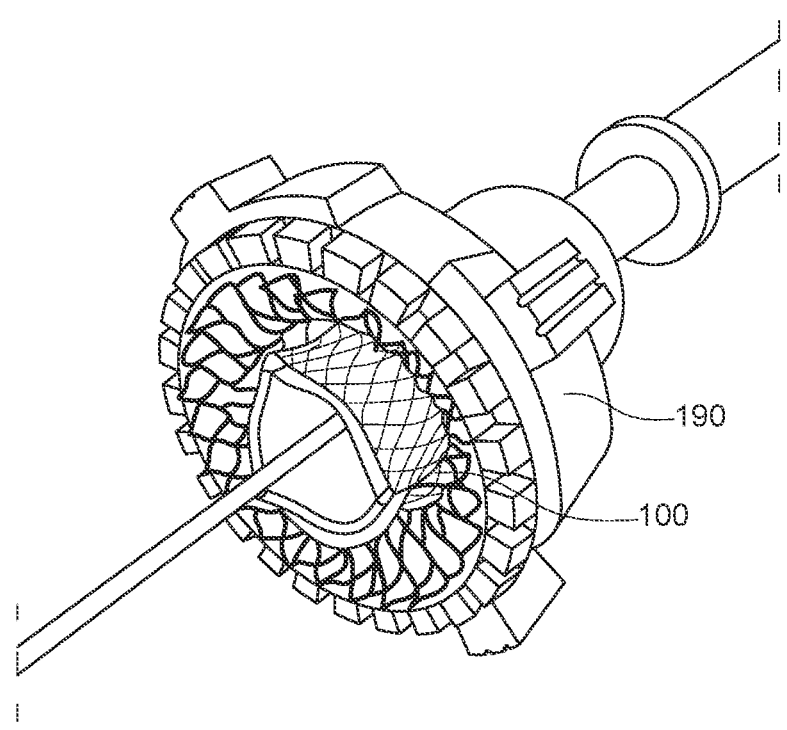
Figure 10L:
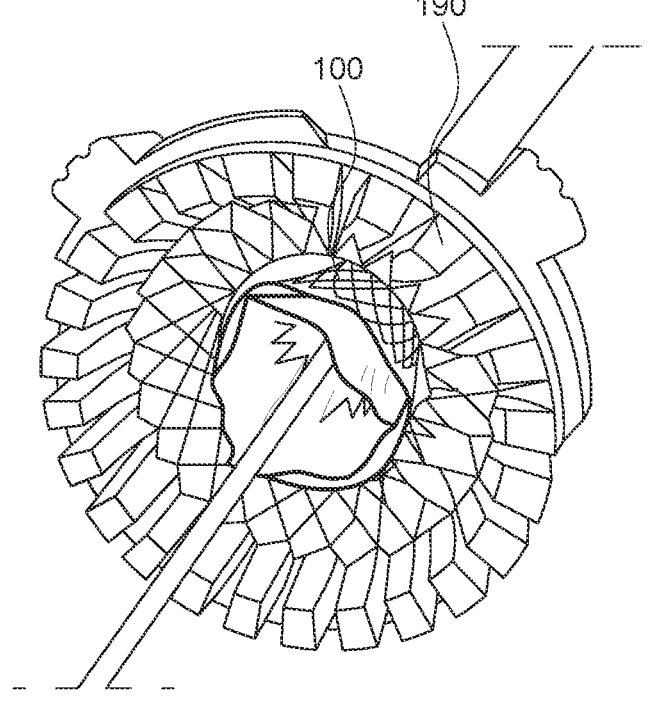
Figure 10M:
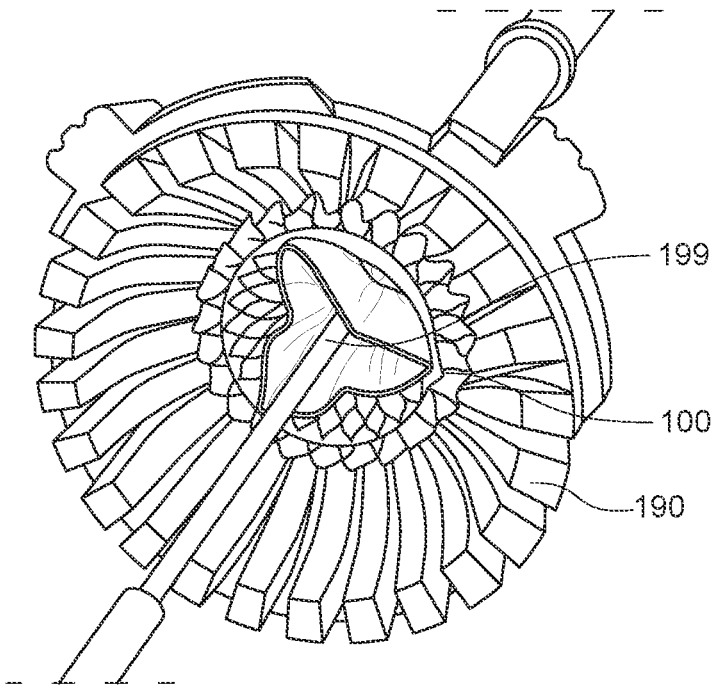
Figure 10N:
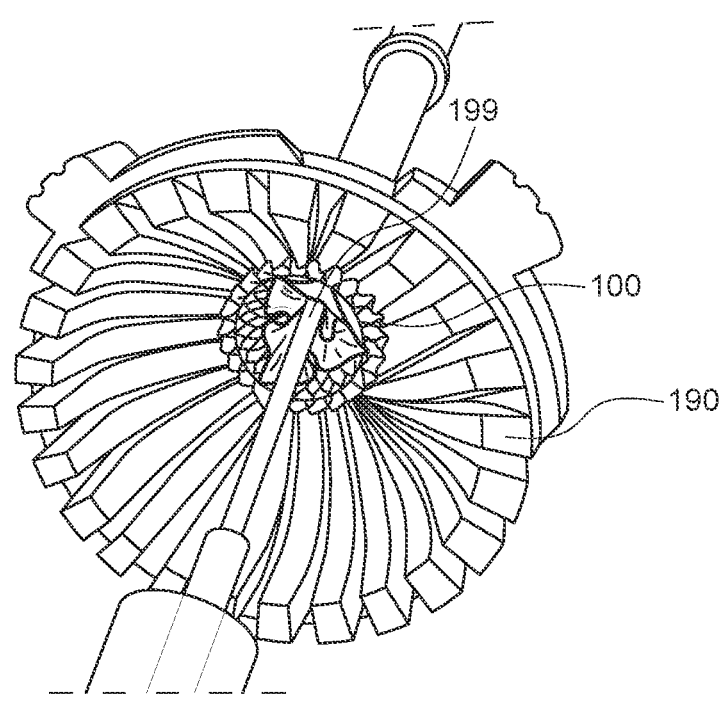
Figure 10O:
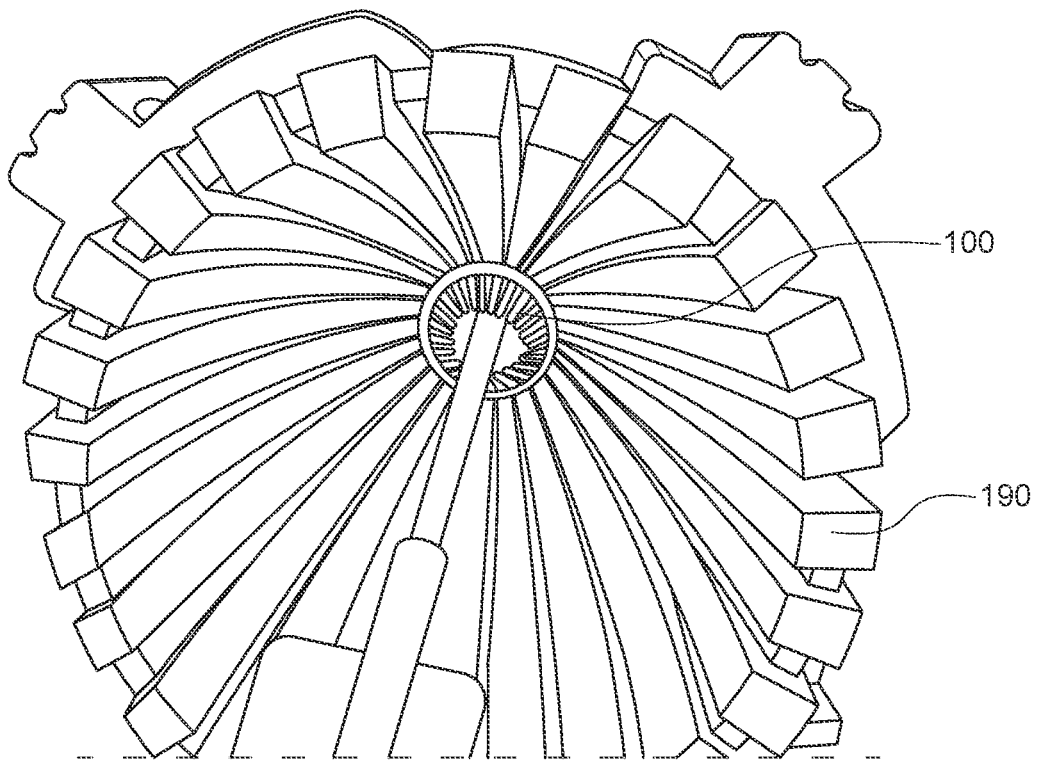

FIGS. 10A-10O illustrate various steps of removing a fully assembled packaging assembly 50 from its packaging and transferring replacement valve 100 from the packaging assembly to a delivery device according to embodiments of the disclosure. An operator or user, such as a surgeon, may remove packaging assembly 50 from packaging 55 by holding onto at least one rib 171 as shown in FIG. 10A, and may submerge the packaging assembly into a liquid such as saline 56 to rinse or wet the assembly, as shown in FIG. 10B. It should be understood that packaging 55 may include a seal, cap, or other member that must be removed prior to removing packaging assembly 50 from packaging 55. A guidewire 64 may be inserted into a proximal end of packaging assembly 50, passed through exit end 192 of funnel 190, and further passed through rod 178 and pin 182 as shown in FIG. 10C. Guidewire 64 may help to align retention mechanism 180 with a receiving component of delivery device 60 to maintain the coaxial nature of cap 186 and the lumen of the delivery device when replacement heart valve 100 is being connected to the delivery device. Guidewire 64 may extend from an interior lumen of suture catheter 62 which may extend from an interior lumen of delivery device 60 as shown in FIG. 10D, and the suture catheter may be inserted through exit end 192 of funnel 190 to couple to retention mechanism 180 using guidewire 64 for ease of alignment. In other words, the suture catheter 62 may ride over the guidewire 64 until a distal tip of the suture catheter abuts or contacts the cap 186. Packaging assembly 50 is then threadably attached to delivery device 60 by threading the distal tip of suture catheter 62 over cap 186 of retention mechanism 180. Exemplary methods of attaching the delivery system to the replacement heart valve are described in U.S. Patent Publication No. 2018/0092744, the disclosure of which is hereby incorporated by reference herein.

After coupling suture catheter 62 to retention mechanism 180, the suture catheter may be retracted proximally (i.e., toward delivery device 60) as shown in FIG. 10E, and funnel 190 may be positioned over delivery device 60 as shown in FIG. 10F so that the funnel is fixed relative to the delivery device during loading of the valve into the delivery device. As described above, delivery device 60 may engage with packaging assembly 50 such that the delivery device is inserted into the cylindrical indentation of funnel and a distal flange 65 of the delivery device abuts the corresponding cylindrical indentation of funnel 190. Further, lumen 193 of funnel 190 at exit end 192 is aligned with a lumen of the delivery device to allow for a smooth transition of valve 100 from the funnel to the delivery device. Once funnel 190 is positioned to abut delivery device 60, suture catheter 62 may be further retracted proximally to pull cap 186 and sutures 188 of retention mechanism 180 and cause valve 100 to apply a degree of pressure onto the inner surface of funnel 190. Valve support 160 may be decoupled from funnel 190 in the manner described above. That is, the user may rotate valve support 160 relative to funnel 190 in a direction to overcome the snap fit and transition the valve support from a locked configuration to an unlocked configuration, as shown in FIGS. 10G and 10H. Valve support 160 may be removed distally, e.g., in a direction away from the delivery device 60. It should be noted that valve support 160 may be decoupled from funnel 190 before or after valve 100 has been translated through the funnel and loaded into delivery device 60. It should also be noted that in examples of packaging assembly 50 including ring 140, the ring may be disassembled and removed from the packaging assembly at any time after suture catheter 62 is coupled to retention mechanism 180 and retracted to cause replacement heart valve 100 to contact and apply a minimal degree of force against funnel 190.

Suture catheter 62 may then be further retracted proximally into delivery device 60 to pull valve 100 through funnel 190 via sutures 188 as shown in FIG. 10I. Valve 100 may be oriented such that each tine 107 aligns with a corresponding slot 194 in funnel 190, as shown in FIG. 10J, and the radial alignment of the valve may be maintained by the slots and grooves 177 on the inner surface of the funnel as the valve is translated therethrough. As described above, valve 100 is translated through the tapering diameter of funnel 190, thereby transitioning valve from the expanded condition to the collapsed condition (or substantially collapsed) upon reaching exit end 192 of the funnel. In some examples, an internal support member 199 may be used to assist in the uniform collapse of valve 100, as shown in FIGS. 10M-10N. FIGS. 10K-10O show valve 100 in stages being translated through funnel 190 and transitioning from the expanded condition to the collapsed condition. As illustrated in FIG. 10O, valve 100 is in a substantially collapsed condition in which it is sized to pass through exit end 192 of funnel 190. Catheter 62 may be further retracted until valve 100 has transitioned from positioning within funnel 190 to being positioned within the lumen of delivery device 60 in the collapsed condition for delivery.

Figure 11A:
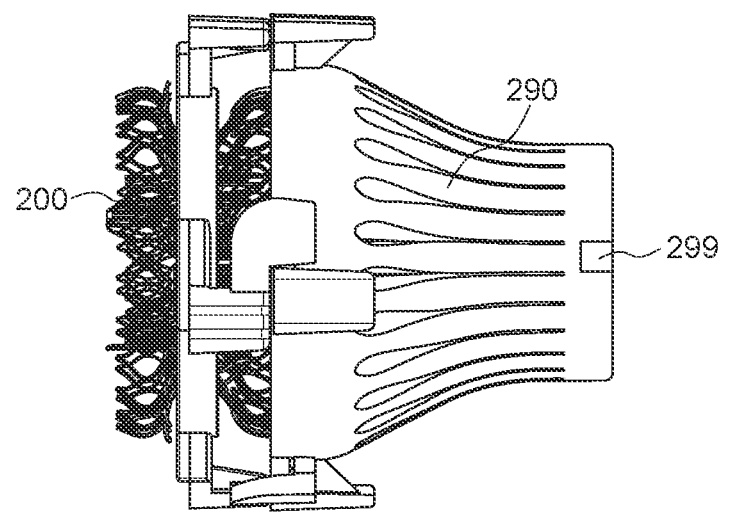
FIG. 11A is a side view of a packaging assembly according to another embodiment of the disclosure.
Figure 11B:
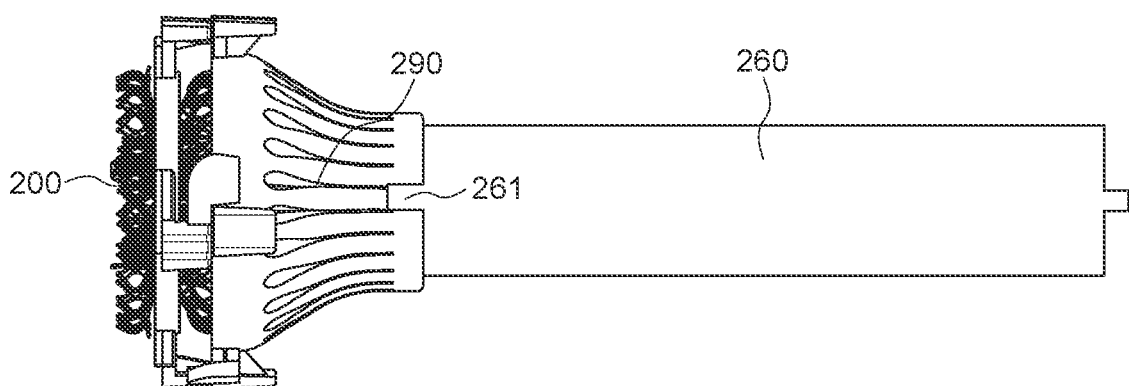
FIG. 11B is a side schematic view of the packaging assembly of FIG. 11A mated with a delivery device.

In some examples, a prosthetic heart valve may be modified from the embodiment of the valve described above. For example, a valve may include a region without tines protruding from the valve, or a valve may have less skirt coverage on the ventricular side of the stent, for instance, to reduce or minimize obstructions in the left ventricular outflow tract ("LVOT") following implantation of the valve. As such, a prosthetic heart valve may be rotationally asymmetric. To accommodate such examples, a funnel 290, shown in FIG. 11A, may include a recess 299 along the circumference of exit end 292, the recess 299 adapted to mate with a protrusion 261 on delivery device 260 to rotationally align the funnel 290 to delivery device 260 as shown in FIG. 11B. The prosthetic heart valve 200 may be loaded into the funnel such that the irregular portion of the valve (e.g., the portion lacking tines, having less skirt coverage, etc.) may be loaded in a certain position, such as being circumferentially aligned with the recess 299 of the funnel 290, and the recess 299 of the funnel 290 may be mated with the protrusion 261 of the delivery device 260 to align the valve 200, funnel 290 and delivery device 260 and thereby maintain alignment of the components as the valve is translated through the funnel and into the delivery device.

According to one aspect of the disclosure, a system for heart valve replacement comprises:

a collapsible and expandable replacement heart valve; and a packaging assembly for storing the replacement heart valve, the packaging assembly including:

a funnel extending from a first end to a second end, the funnel having a first interior diameter at the first end and a second interior diameter at the second end, the second interior diameter being smaller than the first interior diameter, the funnel defining an internal lumen extending between the first and second ends, the funnel defining a plurality of longitudinal slots extending along an interior surface of the funnel between the first and second ends; and/or the plurality of longitudinal slots are circumferentially spaced around the interior surface of the funnel; and/or the plurality of longitudinal slots are equidistantly spaced around the interior surface of the funnel; and/or the funnel has a first circumference at the first end and a second circumference at the second end, each slot having a first end positioned a spaced distance from the first circumference, and a second end positioned at the second circumference; and/or each slot has a width which tapers as the slot extends between the first and second ends; and/or the funnel has a wall thickness, and the plurality of longitudinal slots extend through the entire wall thickness of the funnel; and/or the interior surface of the funnel defines a plurality of grooves extending between the first and second ends of the funnel, each groove positioned between an adjacent pair of the plurality of longitudinal slots; and/or a valve support having a base for holding the replacement heart valve; and/or a ring sized and shaped to fit within the valve support and around a circumference of the replacement heart valve; and/or the ring includes a first ring portion and a second ring portion adapted to be detachably coupled to each other to form the ring; and/or the first ring portion includes a first protrusion and a first aperture and the second ring portion includes a second protrusion and a second aperture, wherein the first protrusion is sized and shaped to fit in the second aperture and the second protrusion is sized and shaped to fit in the first aperture; and/or a retention mechanism including a cap and a plurality of sutures having a first end attached to the cap and a second end configured to be attached to the replacement heart valve; and/or the funnel defines a recess along a circumference of the second end, the recess configured to mate with a protrusion on a delivery device.

According to another aspect of the disclosure, a packaging assembly for packaging a collapsible and expandable replacement heart valve comprises:

a valve support having a base;

a funnel detachably coupleable to the valve support, the funnel defining a lumen configured to receive the replacement heart valve; and a retention mechanism including a pin extending through a lumen of the valve support and a plurality of sutures attached to the pin, wherein the plurality of sutures are configured to be attached to the replacement heart valve; and/or the packaging assembly has an unlocked configuration in which the funnel and valve support are detached, and a locked configuration in which the funnel and valve support are locked together; and/or in the locked configuration, the funnel and the valve support are rotationally and axially locked to one another; and/or the packaging assembly transitions between the unlocked and locked configurations by rotation of at least one of the funnel and the valve support relative to the other; and/or in the locked configuration, the funnel and the valve support are locked together by a snap-fit connection; and/or the funnel includes at least one securement member extending radially outward from a circumference of the funnel; and/or the valve support includes a ledge projecting radially inward from the base to define a groove for receiving a respective one of the at least one securement member; and/or the funnel includes four securement members and the valve support includes four grooves for receiving the securement members; and/or each of the securement members includes a groove on a proximal surface of the securement member sized and shaped to receive a protrusion extending from the ledge of the valve support; and/or a ring detachably coupleable to the valve support and the funnel, the ring configured to be positioned within the valve support and configured to fit around a circumference of the replacement heart valve; and/or the ring includes a first ring portion and a second ring portion detachably coupled to each other to form the ring; and/or the packaging assembly has an unlocked configuration, in which the valve support, the ring, and the funnel are detached, and a locked configuration in which the valve support, the ring, and the funnel are locked together; and/or in the locked configuration, the valve support, the ring, and the funnel are rotationally and axially locked to one another; and/or the packaging assembly transitions between the locked configuration and a partially locked configuration by rotation of at least one of the valve support, the ring, and the funnel relative to another; and/or the packaging assembly transitions between a partially locked configuration and the unlocked configuration by rotation of at least one of the valve support, the ring, and the funnel relative to another; and/or in the locked configuration, the valve support and the ring are locked together by a snap-fit connection, and the ring and the funnel are locked together by a snap-fit connection.

According to another aspect of the disclosure, a system for heart valve replacement comprises:

a packaging assembly for storing a collapsible and expandable replacement heart valve, the packaging assembly including:

a funnel extending from a first end to a second end, the funnel having a first inner diameter at the first end and a second inner diameter at the second end, the second inner diameter being smaller than the first inner diameter, the funnel defining an internal lumen extending between the first and second ends, the funnel defining a plurality of longitudinal slots extending along an inner surface of the funnel between the first and second ends; and/or a valve support having a base for holding the replacement heart valve; and/or a retention mechanism including a cap and a plurality of sutures attached to the cap and configured to be attached to the replacement heart valve; and/or the packaging assembly has a locked configuration in which the funnel and the valve support are locked together and the plurality of sutures are under tension; and/or the replacement heart valve includes a plurality of tines extending radially outward, and the replacement valve is oriented within the funnel such that each tine aligns with a corresponding slot.

According to a method of packaging a replacement heart valve, the method comprises:

positioning the replacement heart valve within a funnel;

coupling the funnel to a valve support; and coupling a retention mechanism to the replacement heart valve to hold the valve in position relative to the valve support and the funnel, wherein the replacement heart valve, the funnel, the valve support, and the retention mechanism together form a packaging assembly; and/or coupling the funnel to the valve support includes abutting a distal surface of the funnel against a proximal surface of the valve support and rotating the funnel relative to the valve support in a locking direction to engage ledges of the valve support with corresponding securement members of the funnel; and/or coupling the retention mechanism to the replacement heart valve includes providing a plurality of sutures having a first end attached to a cap of the retention mechanism and a second end, coupling the second ends of the plurality of sutures to corresponding attachment members of the replacement heart valve, and positioning the valve such that the plurality of sutures are under tension; and/or the slots of the funnel define a depth such that the plurality of tines do not scrape a surface of the funnel while the replacement heart valve is translated through the funnel.

According to another aspect of the disclosure, a method of packaging a replacement heart valve comprises:

positioning the replacement heart valve within a ring such that the ring circumferentially surrounds a central portion of the replacement heart valve;

coupling the ring to a funnel by engaging locking tabs of the ring with corresponding securement members of the funnel; and coupling the ring to a valve support by engaging locking tabs of the ring with corresponding ledges of the valve support.

According to another aspect of the disclosure, a method of loading a replacement heart valve from a packaging assembly into a delivery device comprises the steps of:

providing a packaging assembly including a replacement heart valve positioned within a funnel, the replacement heart valve having a plurality of tines aligned with corresponding slots of the funnel;

coupling the packaging assembly to the delivery device;

translating the replacement heart valve through the funnel and the tines through the slots to collapse the replacement heart valve from an expanded condition to a collapsed condition; and transitioning the replacement heart valve from the funnel to the delivery device; and/or the step of translating the replacement heart valve includes coupling a suture catheter of the delivery device to a retention mechanism of the packaging assembly; and/or the step of coupling the packaging assembly to the delivery device includes inserting a distal flange of the delivery device into a cylindrical indentation of the funnel.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for heart valve replacement comprising:
a collapsible and expandable replacement heart valve, wherein the replacement heart valve includes a plurality of tines extending radially outward; and
a packaging assembly for storing the replacement heart valve, the packaging assembly comprising:
a funnel extending from a first end to a second end, the funnel having a first interior diameter at the first end and a second interior diameter at the second end, the second interior diameter being smaller than the first interior diameter, the funnel defining an internal lumen extending between the first and second ends, the funnel defining a plurality of longitudinal slots extending along an interior surface of the funnel between the first and second ends,
wherein each of the plurality of longitudinal slots defines a depth such that free ends of the plurality of tines do not scrape an interior surface of the funnel while the replacement heart valve is translated through the funnel, wherein when the replacement heart valve is received within the funnel, each of the plurality of tines aligns with a corresponding one of the plurality of longitudinal slots.

2. The system of claim 1, wherein the plurality of longitudinal slots are one of: circumferentially spaced around the interior surface of the funnel, or equidistantly spaced around the interior surface of the funnel.

3. The system of claim 1, wherein the funnel has a first circumference at the first end and a second circumference at the second end, each slot having a first end positioned a spaced distance from the first circumference, and a second end positioned at the second circumference.

4. The system of claim 1, wherein each slot has a width which tapers as the slot extends between the first and second ends.

5. The system of claim 1, wherein the funnel has a wall thickness, and the plurality of longitudinal slots extend through the entire wall thickness of the funnel.

6. The system of claim 1, wherein the interior surface of the funnel defines a plurality of grooves extending between the first and second ends of the funnel, each groove positioned between an adjacent pair of the plurality of longitudinal slots.

7. The system of claim 1, further comprising a valve support having a base for holding the replacement heart valve.

8. The system of claim 7, further comprising a ring sized and shaped to fit within the valve support and around a circumference of the replacement heart valve.

9. The system of claim 8, wherein the ring includes a first ring portion and a second ring portion adapted to be detachably coupled to each other to form the ring.

10. The system of claim 9, wherein the first ring portion includes a first protrusion and a first aperture and the second ring portion includes a second protrusion and a second aperture, wherein the first protrusion is sized and shaped to fit in the second aperture and the second protrusion is sized and shaped to fit in the first aperture.

11. The system of claim 1, further comprising a retention mechanism including a cap and a plurality of sutures having a first end attached to the cap and a second end configured to be attached to the replacement heart valve.

12. The system of claim 1, wherein the funnel defines a recess along a circumference of the second end, the recess configured to mate with a protrusion on a delivery device.

13. The system of claim 1, wherein the funnel has a wall thickness, and the plurality of longitudinal slots extend through part of the wall thickness of the funnel.

* * * * *